United States Patent
Chow et al.

(10) Patent No.: US 7,031,776 B2
(45) Date of Patent: Apr. 18, 2006

(54) METHODS FOR IMPROVING DAMAGED RETINAL CELL FUNCTION

(75) Inventors: Alan Y. Chow, Wheaton, IL (US); Vincent Y. Chow, Hanover Park, IL (US)

(73) Assignee: Optobionics, Naperville, IL (US)

( * ) Notice: Subject to any disclaimer, the term of this patent is extended or adjusted under 35 U.S.C. 154(b) by 539 days.

(21) Appl. No.: 10/056,793

(22) Filed: Jan. 23, 2002

(65) Prior Publication Data

US 2003/0014089 A1  Jan. 16, 2003

Related U.S. Application Data

(60) Provisional application No. 60/301,877, filed on Jun. 29, 2001.

(51) Int. Cl.
*A61N 1/05* (2006.01)

(52) U.S. Cl. .................................................. 607/54

(58) Field of Classification Search ................ 600/373, 600/393; 607/50, 53, 54, 116; 623/6.63
See application file for complete search history.

(56) References Cited

U.S. PATENT DOCUMENTS

| | | |
|---|---|---|
| 2,760,483 A | 8/1956 | Tassicker |
| 3,594,823 A | 7/1971 | Collins |
| 3,628,193 A | 12/1971 | Collins |
| 3,766,311 A | 10/1973 | Boll |
| 3,848,608 A | 11/1974 | Leonard |
| 3,914,800 A | 10/1975 | Collins |
| 4,001,867 A | 1/1977 | Kravitz et al. |
| 4,211,474 A | 7/1980 | Le Goff |
| 4,251,887 A | 2/1981 | Anis |
| 4,272,910 A | 6/1981 | Danz |
| 4,551,149 A | 11/1985 | Sciarra |
| 4,600,004 A | 7/1986 | Lopez et al. |
| 4,601,545 A | 7/1986 | Kern |
| 4,628,933 A | 12/1986 | Michelson |
| 4,679,572 A | 7/1987 | Baker, Jr. |
| 4,750,498 A | 6/1988 | Graham |
| 4,810,050 A | 3/1989 | Hooper |
| 4,832,202 A | 5/1989 | Newman et al. |
| 4,873,448 A | 10/1989 | Shirai |

(Continued)

FOREIGN PATENT DOCUMENTS

DE  195 29 371 C2  2/1997

(Continued)

OTHER PUBLICATIONS

A. Y. Chow, G.A. Peyman, J. Pulido, *"Safety and Feasibility of Subretinal Artificial Silicon Retina™ Retinal Prosthesis for the Treatment of Patients with Retinitis Pigmentosa"*, ARVO (The Association of Research in Vision and Ophthalmology), Abstract Issue of Annual Meeting, For Lauderdale, Florida, Apr. 29-May 4, 2001, Abstract 5042-11:11 (1 page and cover page), Published Mar. 15, 2001.

(Continued)

*Primary Examiner*—Robert E. Pezzuto
*Assistant Examiner*—Frances P. Oropeza
(74) *Attorney, Agent, or Firm*—Brinks Hofer Gilson & Lione

(57) ABSTRACT

Methods of using electrical stimulation by itself or in conjunction with growth factors to treat and prevent visual loss due to choroidal, retinal pigment epithelial and/or neuroretinal cell degeneration and dysfunction are presented.

8 Claims, 13 Drawing Sheets

U.S. PATENT DOCUMENTS

| | | | |
|---|---|---|---|
| 4,978,842 A | 12/1990 | Hinton et al. | |
| 5,016,633 A | 5/1991 | Chow | |
| 5,024,223 A | 6/1991 | Chow | |
| 5,109,844 A | 5/1992 | de Juan, Jr. et al. | |
| 5,130,528 A | 7/1992 | Phillips, Jr. | |
| 5,130,776 A | 7/1992 | Popovic et al. | |
| 5,159,927 A | 11/1992 | Schmid | |
| 5,223,728 A | 6/1993 | Gempe | |
| 5,256,882 A | 10/1993 | Miyasaka | |
| 5,338,991 A | 8/1994 | Lu | |
| 5,351,309 A | 9/1994 | Lee et al. | |
| 5,397,350 A | 3/1995 | Chow et al. | |
| 5,411,540 A | 5/1995 | Edell et al. | |
| 5,476,494 A | 12/1995 | Edell et al. | |
| 5,491,349 A | 2/1996 | Komoto et al. | |
| 5,556,423 A * | 9/1996 | Chow et al. | 623/6.63 |
| 5,648,655 A | 7/1997 | Rostoker | |
| 5,717,201 A | 2/1998 | Lin et al. | |
| 5,837,995 A | 11/1998 | Chow et al. | |
| 5,865,839 A | 2/1999 | Doorish | |
| 5,895,414 A | 4/1999 | Sanchez-Zambrano | |
| 5,895,415 A | 4/1999 | Chow et al. | |
| 5,935,155 A | 8/1999 | Humayun et al. | |
| 5,944,747 A | 8/1999 | Greenberg et al. | |
| 6,032,062 A | 2/2000 | Nisch | |
| 6,035,236 A | 3/2000 | Jarding et al. | |
| 6,066,675 A | 5/2000 | Wen et al. | |
| 6,230,057 B1 | 5/2001 | Chow et al. | |
| 6,298,270 B1 | 10/2001 | Nisch et al. | |
| 6,324,429 B1 | 11/2001 | Shire et al. | |
| 6,347,250 B1 | 2/2002 | Nisch et al. | |
| 6,389,317 B1 | 5/2002 | Chow et al. | |
| 6,393,327 B1 | 5/2002 | Scribner | |
| 6,549,808 B1 * | 4/2003 | Gisel et al. | 607/53 |
| 2002/0147464 A1 | 10/2002 | Peyman | |

FOREIGN PATENT DOCUMENTS

| | | |
|---|---|---|
| EP | 0 084 621 A2 | 11/1982 |
| EP | 0 233 789 | 8/1987 |
| EP | 0 501 904 A2 | 9/1992 |
| GB | 2 229 543 A | 9/1990 |

OTHER PUBLICATIONS

Copy of International Search Report for PCT/US02/20557 dated May 1, 2003.

Wen, R. et al., "Injury-Induced Upregulation of bFGF and CNTF mRNAS in the Rat Retina", *The Journal of Neuroscience,* Nov. 1995, pp. 7377-7385.

Copy of International Search Report for corresponding PCT/US02/20808 dated Mar. 21, 2003.

Majji, Ajit, et al.: "Long Term Histological and Electrophysiological Results of an Inactive Epiretinal Electrode Array Implantation in Dogs", Investigative Opthalmology & Visual Science, Aug. 1999, vol. 40, No. 9, pp. 2073-2081.

Margalit, et al.: "Bioadhesives for Intraocular Use", Retina, The Journal of Retinal and Vitreous Diseases, 2000, vol. 20, No. 5, pp. 469-477.

Peyman, Gholam, MD, et al.: "Subretinal Semiconductor Microphotodiode Array", Ophthalmic Surgery and Lasers, Mar. 1998, vol. 29, No. 3, pp. 234-241.

Abrams, Dr. Susan B., "Implanted photodiodes could restore lost vision", *Biophotonics Research,* 1997, 2 pages.

Acheson, A., P.A. Barker, R.F. Alderson, F.D. Miller, et al., "Detection of Brain-Derived Neurotrophic Factor-Like Activity in Fibroblasts and Schwann Cells: Inhibition by Antibodies to NGF", *Neuron,* vol. 7, 1991, pp 265-75.

Ando, Haruhisa, et al. "Design Consideration and Performance of a New MOS Imaging Device", *IEEE,* 1985, 6 pages.

Armington, J.C., Brigell, M., "Effects of Stimulus Location and Pattern Upon the Visually Evoked Cortical Potential and the Electroretinogram," *Intern. J. Neuroscience,* vol. 14, 1981, pp 169-178.

Baylor, D.A., Fuortes, M.G.F., "Electrical Responses of Single Cones in the Retina of the Turtle," *J. Physiol,* vol. 207, 1970, pp 77-92.

Bergmann-Schaefer, "Lehrbuch der Experimentalphysik" (Textbook of Experimental Physics), vol. II, "Electricity and Magnetism" by Prof. Dr. -Ing. H. Gobrecht, 1971, 3 pp. plus translation.

Bobsch, M.D., Joseph M. and Grosser, Ph.D., Morton "Newer Repair at the AXOM Level: A Merger of Microsurgery and Microelectronics," VCH Publishers, Inc., 1967.

Boettner, E.A., Wolter, J.R., "Transmission of the Ocular Media," *Investigative Ophthalmology,* vol. 1, 1962, pp 776-783.

Bosco, A., and Linden, R., "BDNF and NT-4 Differentially Modulate Neurite Outgrowth in Developing Retinal Ganglion Cells", *J Neurosci Res.* vol. 57, 1999, pp 759-69.

Brady, G.S., Clauser, H.R., *Materials Handbook, Thirteenth Edition,* New York, McGraw-Hill, 1991, pp 739-740.

Brindley, G.S., "The Site of Electrical Excitation of the Human Eye," *J. Physiol,,* vol. 127, 1955, pp 189-200.

Brindley, G.S., "Beats Produced by Simultaneous Stimulation of the Human Eye with Intermittent Light and Intermittent or Alternating Electric Current," *J. Physiol.,* vol. 164, 1962, pp 156-167.

Brown, M.G. et al., "Monolithically Integrated 1×12 Array of Planar InGaAs/InP Photodiodes," *Journal of Lightwave Technology,* vol. LT-4, No. 3, Mar. 1986, pp. 283-286.

Caleo, M., Lodovichi, C., and Maffei, L., "Effects of Nerve Growth Factor on Visual Cortical Plasticity Require Afferent Electrical Activity", *Eur. J. Neurosci.,* vol. 11, 1999, pp 2979-84.

Carmignoto, G., Maffei, L., Candeo, P., Canella, R. and Comelli, C., "Effect of NGF on the Survival of Rat Retinal Ganglion Cells Following Optic Nerve Section", *J. Neurosci.,* vol. 9, 1989, pp 1263-72.

Chapin, D.M., et al., "A New Silicon *p-n* Junction Photocell for Converting Solar Radiation into Electrical Power," Letters to the Editor, Journal of Applied Physics, vol. 25, 1954, pp 676-7.

Chow, A.Y., "Electrical Stimulation of the Rabbit Retina with Subretinal Electrodes and High Density Microphotodiode Array Implants," ARVO Abstracts, *Invest. Ophthalmol. Vis. Sci.* 199334 (Suppl), p. 835.

Chow, A.Y., Pardue, M.T., Chow, V.Y., Peyman, G.A., et al., "Implantation of Silicon Chip Microphotodiode Arrays into the Cat Subretinal Space", *IEEE Trans. Neu. Syst. Rehabil. Eng.,* vol. 9, 2001, pp 86-95.

Chow, A.Y., and Chow, V.Y., "Subretinal Electrical Stimulation of the Rabbit Retina", *Neurosci. Lett.* vol. 225, 1997, pp 13-16.

Chow, A.Y., and Peachey, N., "The Subretinal Microphotodiode Array Retinal Prosthesis II", *Ophthal. Res.,* vol. 31, 1999, p. 246.

Cui, Q., So, K.F., and Yip, H.K., "Major Biological Effects of Neurotrophic Factors on Retinal Ganglion Cells in Mammals", *Biol. Sig. Recept.,* vol. 7, 1998, pp 220-226.

Curcio, C.A., Sloan, K.R., Kalina, R.E., Hendrickson, A.E., "Human Photoreceptor Topography,", *J Comp. Neuro.*, vol. 292, 1990, pp 497-523.

Dawson, W.W., Radtke, N.D., "The Electrical Stimulation of the Retina by Indwelling Electrodes," *Invest. Ophthalmol. Visual Sci.*, vol. 16, 1997, pp 249-252.

Dooley, D.M., Sharkey, J., Keller, W., and Kasprak, W., "Treatment of Demyelinating and Degenerative Diseases by Electro Stimulation of the Spinal Cord", *Med. Prog. Technol.*, vol. 6, 1978, pp 1-14.

Dowling, J.E., Ripps, H., Visual Adaptation in the Retina of the Skate, *J Gen Physiol.*, vol. 56, 1970, pp 491-520.

Eagle, R.C., Lucier, A.C., Bernardino, V.B., et al., "Retinal Pigment Epithelial Abnormalities in Fundus Flavimaculatus," *Ophthalmol.*, vol. 87, 1980; pp 1189-1200.

Evans, R.D., Foltz, D., and Foltz, K., "Electrical Stimulation with Bone and Wound Healing", *Clin. Podiatr. Med. Surg.*, vol. 18, 2001, pp 79-95.

Gibiliscos, S., and Sclater, N., Encyclopedia of Electronics, 2d Ed., 1990, pp. 640-645.

Fenwick, P.B.C., Stone, S.A., Bushman, J., Enderby, D., "Changes in the Pattern Reversal Visual Evoked Potential as a Function of Inspired Nitrous Oxide Concentration," *Electroencephalogr. Clin. Neurophysiol.*, vol. 57, 1984, pp 57178-183.

John B. Flynn, et al. "Total Active Area Silicon Photodiode Array", 1964, 3 pages.

Frasson, M., Picaud, S., Leveillard, T., Simonutti, M., et al., "Glial Cell Line-Derived Neurotrophic Factor Induces Histologic and Functional Protection of Rod Photoreceptors in rd/rd Mouse", *Invest. Ophthalmol. Visual Sci.*, vol. 40, 1999, pp 2724-34.

Graeme, J., "Position-Sensing Photodiode Amplifiers," Ch. 10, 12 pages.

Granit, R., Helme, T., "Changes in Retinal Excitability Due to Polarization and Some Observations on the Relation Between the Processes in Retina and Nerve," *J. Neurophysiol.*, vol. 2, 1939, pp 556-565.

Hagins, W.A., Penn, R.D., Yoshikami, S., "Dark Current and Photocurrent and Photocurrent in Retinal Rods," J. *Biophys*, vol. 10, 1970, pp 380-412.

Hergert, K., "Detectors: Expanded Photodetector Choices Pose Challenges for Designers", The Photonics Design and Applications Handbook (1996).

Humayun, M.S., Propst, R.H., Hickinbotham, D., de Juan E., Jr., Dagnelie G. "Visual Sensations Produced by Electrical Stimulation of the Retinal Surface In Patients with End-Stage Retinitis Pigmentosa (RP)," ARVO Abstracts, *Invest. Ophthalmol. Vis. Sci.* vol. 34 Suppl, 1993, p. 835.

Humayun, M., Propst R., de Juan, E., et al., "Bipolar Surface Electrical Stimulation of the Vertebrate Retina," *Arch. Ophthalmol.*, vol. 112, 1994, pp 110-116.

Kane, W.J., "Direct Current Electrical Bone Growth Stimulation for Spinal Fusion", *Spine*, vol. 13, 1988, pp 363-365.

Kataoka, S., "An Attempt Towards an Artificial Retina: 3-D IC Technology for an Intelligent Image Sensor," *Transducers '85: International Conference on Solid-State Sensors and Actuators 1985*, pp. 440-442.

Klinke, R., Kral, A., Heid, S., Tillein, J., and Hartmann, R., "Recruitment of the Auditory Cortex in Congenitally Deaf Cats by Long-Term Cochlear Electrostimulation", *Science*, vol. 285, 1999, pp. 1729-1733.

Knighton, R.W., "An Electrically Evoked Slow Potential of the Frog's Retina. I. Properties of Response," *J. Neurophysiol.*, vol. 38, 1975, pp 185-197.

Koyama, S., Haruyama, T., Kobatake, E., and Aizawa, M., "Electrically Induced NGF Production by Astroglial Cells", *Nature Biotechnol.*, vol. 15, 1997, pp 164-166.

Lagey, C.L., Roelofs, J.M., Janssen, L.W.M., Breedijk, M., et al., "Electrical Stimulation of Bone Growth with Direct Current", *Clin. Orthop.*, No. 204, 1986, pp 303-312.

Lambiase, A., and Aloe, L., "Nerve Growth Factor Delays Retinal Degeneration in C3H Mice", *Graefe's Arch. Clin. Exp. Ophthalmol.*, vol. 234, 1996, pp 96-100.

Leake, P.A., Hradek, G.T., and Snyder, R.L., "Chronic Electrical Stimulation by a Cochlear Implant Promotes Survival of Spiral Ganglion Neurons after Neonatal Deafness", *J. Comp. Neurol.*, vol. 412, 1999, pp 543-562.

Leake, P.A., Hradek, G.T., Rebscher, S.J., and Snyder, R.L., "Chronic Intracochlear Electrical Stimulation Induces Selective Survival of Spiral Ganglion Neurons in Neonatally Deafened Cats", *Hear. Res.*, vol. 54, 1991, pp 251-271.

Lin, H-C., et al., "The Vertical Integration of Crystalline NMOS and Amorphous Orientational Edge Detector" IEEE Briefs, 1992, 3 pages.

Melen, R.D., et al., "A Transparent Electrode CCD Image Sensor for a Reading Aid for the Blind," *IEEE Journal of Solid-State Circuits*, vol. SC-9, No.2, Apr. 1974, pp. 41-48.

Narayanan, M.V., Rizzo, J.F., Edell, D., et al., "Development of a Silicon Retinal Implant: Cortical Evoked Potentials Following Focal Stimulation of the Rabbit Retina with Light and Electricity," ARVO Abstracts, *Invest. Ophthalmol. Vis. Sci.*, vol. 35 (Suppl), 1994, p. 1380.

Neely, M.D., and Nicholls, J.G., "Electrical Activity, Growth Cone Motility and the Cytoskeleton", *J. Exp. Biol.* vol. 198, 1995, pp 1433-1446.

Pagon, R.A., "Retinitis Pigmentosa," *Survey Ophthalmol.*, vol. 33, 1988, pp 137-177.

Paton, D., Goldberg, M.F., *Management of Ocular Injuries*, Philadelphia, W.B. Saunders Co., 1976, pp 134-135.

Peachey, N.S., and Chow, A.Y., "Subretinal Implantation of Semiconductor-Based Photodiodes: Progress and Challenges", *J. Rehabil. Res. Develop.*, vol. 36, No. 4, 1999, pp 1-7.

The Penguin Dictionary of Electronics, Editor: Illingworth, V., Young, C., Market House Books Ltd., 1988, pp. 410-413.

Politis, M.J., Zanakis, M.F., and Albala, B.J., "Facilitated Regeneration in the Rat Peripheral Nervous System Using Applied Electric Fields", *J. Trauma.*, vol. 28, 1988, pp 1375-1381.

Politis, M.J., Zanakis, M.F., and Albala, B.J., "Mammalian Optic Nerve Regeneration Following the Application of Electric Fields", *J. Trauma,*, 1988, vol. 28 pp 1548-1552.

Politis, M.J., and Zanakis, M.F., "Short Term Efficacy of Applied Electric Fields in the Repair of the Damaged Rodent Spinal Cord: Behavioral and Morphological Results", *Neurosurgery*, vol. 23, 1988, pp 582-588.

Politis, M.J., and Zanakis, M.F., "The Short-Term Effects of Delayed Application of Electric Fields in the Damaged Rodent Spinal Cord", *Neurosurgery*, vol. 25, 1989, pp 71-75.

Politis, M.J., and Zanakis, M.F., Treatment of the Damaged Rat Hippocampus with a Locally Applied Electric Field:, *Exp. Brain Res.*, vol. 71, 1988, pp 223-226.

Potts, A.M., Inoue J., Buffum D., "The Electrically Evoked Response of the Visual System (EER)," *Invest. Ophthalmol Vis Sci.*, 1968; 7:269-278.

Reh, T.A., McCabe, K., Kelley, M.W., and Bermingham-McDonogh, O., "Growth Factors in the Treatment of Degenerative Retinal Disorders", *Ciba Found. Symp.,* vol. 196, 1996, pp 120-131.

Robblee, L.S., Electrochemical Guidelines for Selection of Protocols and Electrode Materials for Neural Stimulation, Ch. 2, Renner Learning Resource Center (undated), pp 25-66.

Rovamo, J., Virsu, V., "An Estimation and Application of the Human Cortical Magnification Factor," *Exp Brain Res.,* vol. 37, 1979, pp 495-510.

Rubin, M.L., *Optics for Clinicians,* Gainsville, TRIAD Scientific Publishers, 1974, pp 119-123.

Shannon, R.V., "A Model of Safe Levels for Electrical Stimulation," *IEEE Transactions Biomed. Eng.,* vol. 39, 1992, pp 424-426.

Smith, J., "Creating a Bionic Eye", ABC News, Nov. 5, 1998, 3 pages.

Stone, J.L., Barlow, W.E., Humayun, M.S., de Juan, E., Jr., Milam, A.H., "Morphometric Analysis of Macular Photoreceptor and Ganglion Cells in Retinas with Retinitis Pigmentosa," *Arch. Ophthalmol.,* vol. 110, 1992, pp 1634-1639.

Sze, S.M., "Physics of Semiconductor Devices", $2^{nd}$ Ed., A Wiley-Interscience Publication, John Wiley & Sons, (undated).

Tasman, E., ed. *Duane's Foundations of Clinical Ophthamology,* vol. *3,* Philadelphia, Lippincott, 1992; chapter 13:20-25, chapter 60:1-112.

Terr, L.I., Linthicum, F.H., House, W.F., "Histopathologic Study of the Cochlear Nuclei After 10 Years of Electrical Stimulation of the Human Cochlea," *Am. J. Otology.,* vol. 9, 1988, pp 1-7.

Tomita, T., "Electrical Activity of Vertebrate Photoreceptor," *Q. Rev. Biophys.,* vol. 3, 1970, pp. 179-222.

Zrenner, E., et al., "The Development of Subretinal Microphotodiodes for Replacement of Degenerated Photoreceptors", *Ophthalmic Res.,* 1997, pp. 269-280.

Chow, A.Y., and Chow, V.Y., Copy of U.S. Appl. No. 09/564,841 filed on May 4, 2002, 29 pages.

\* cited by examiner

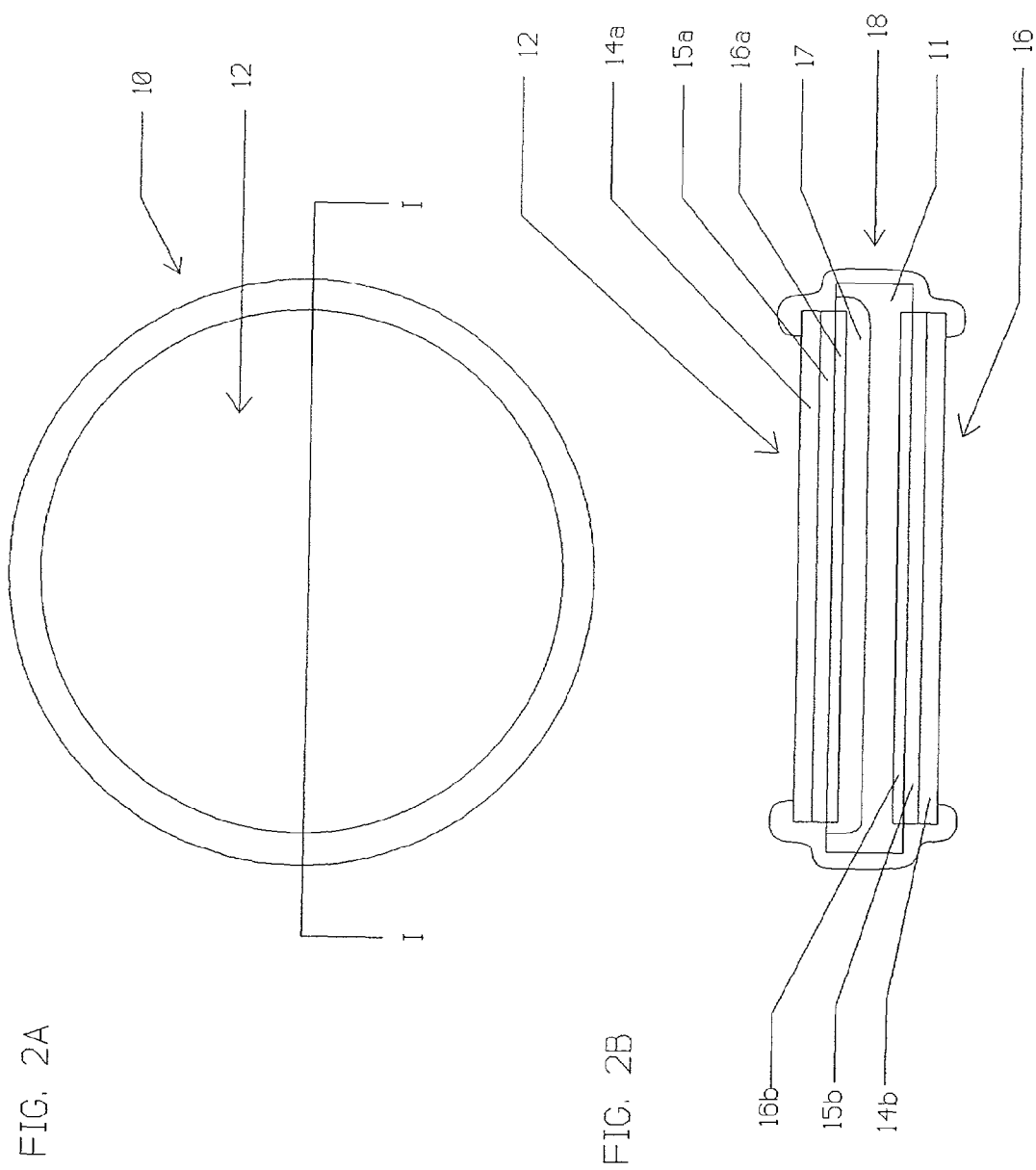

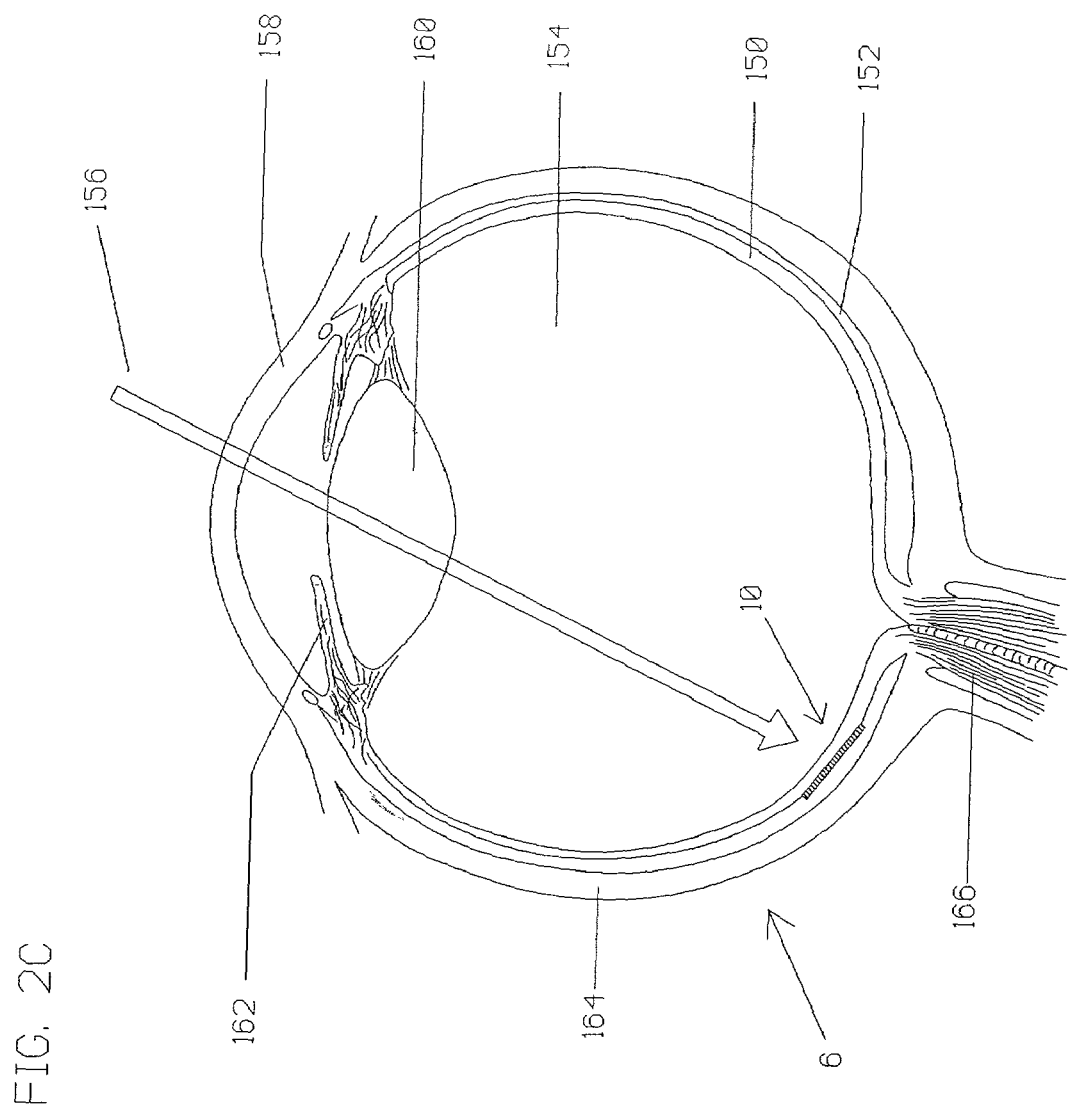

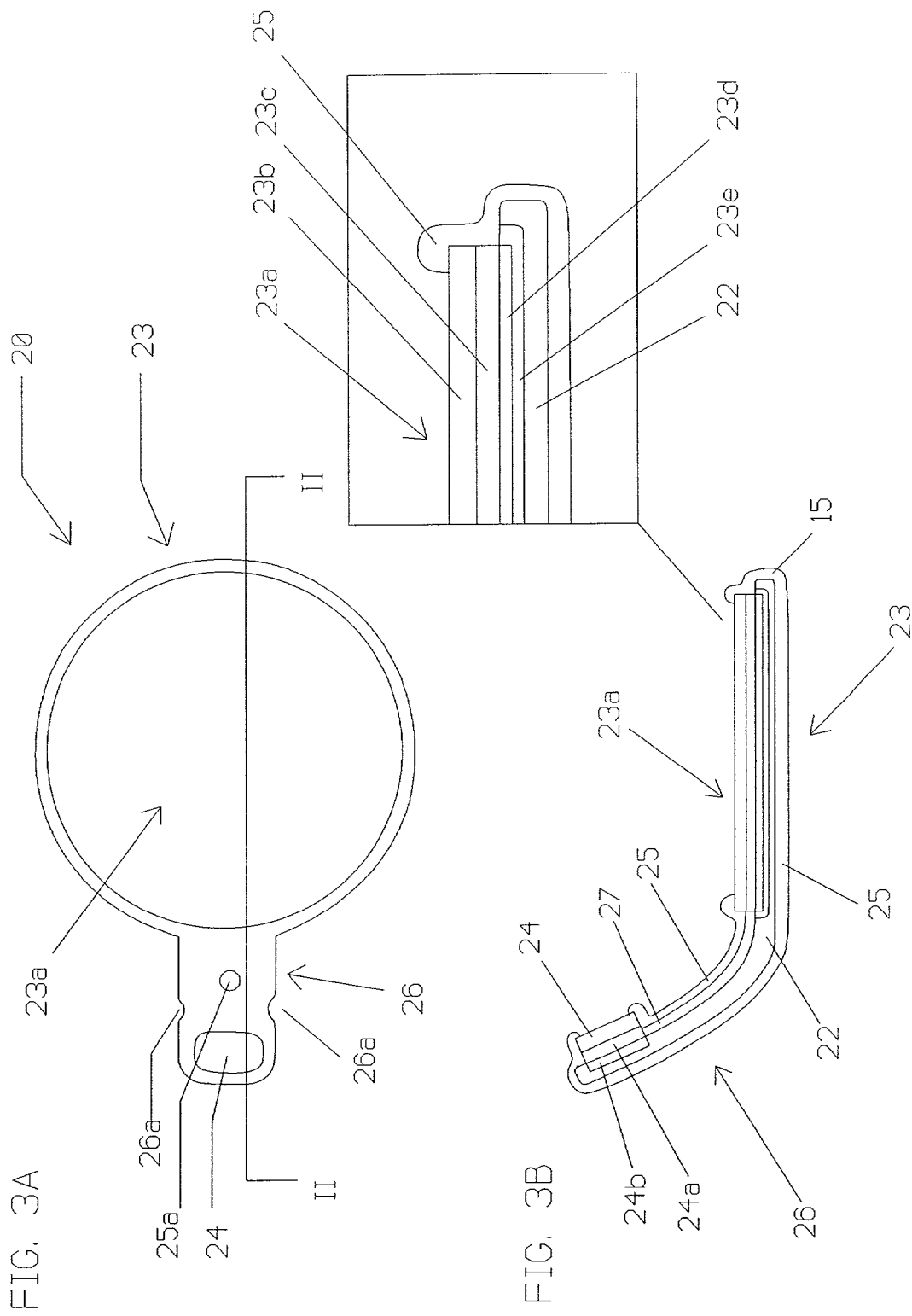

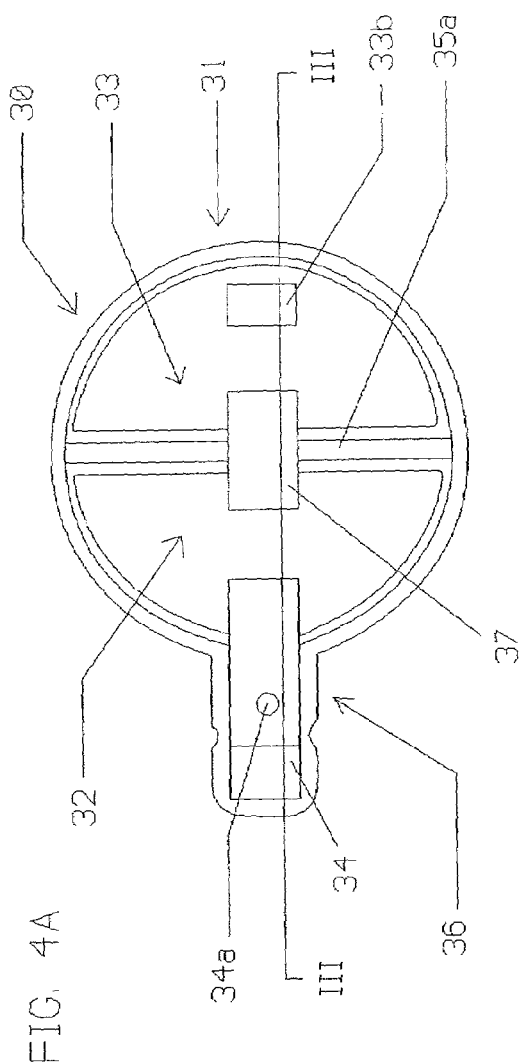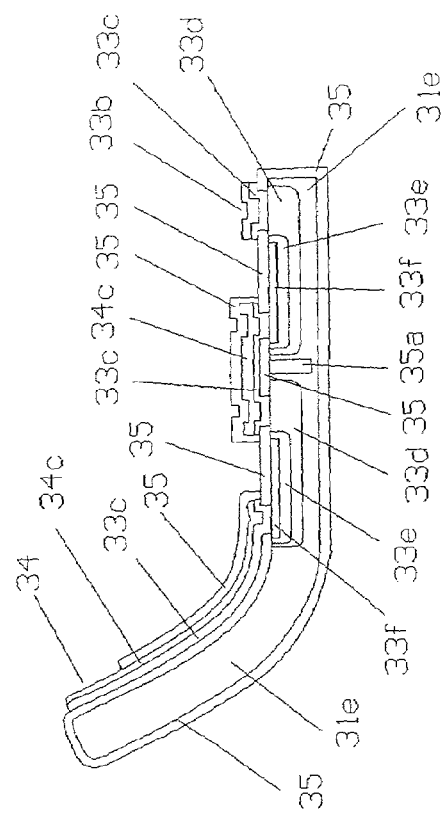
FIG. 4A
FIG. 4B

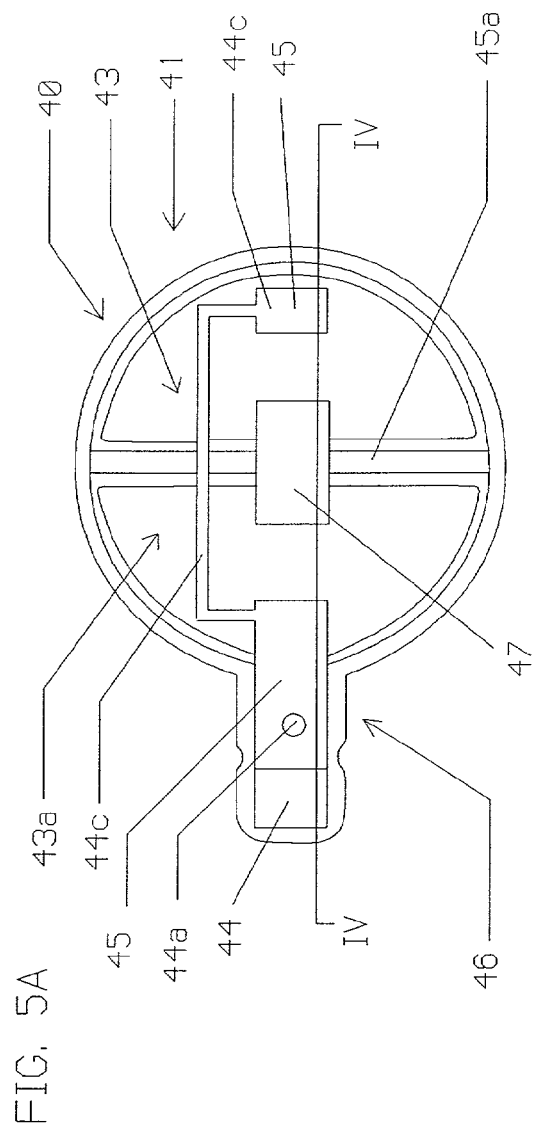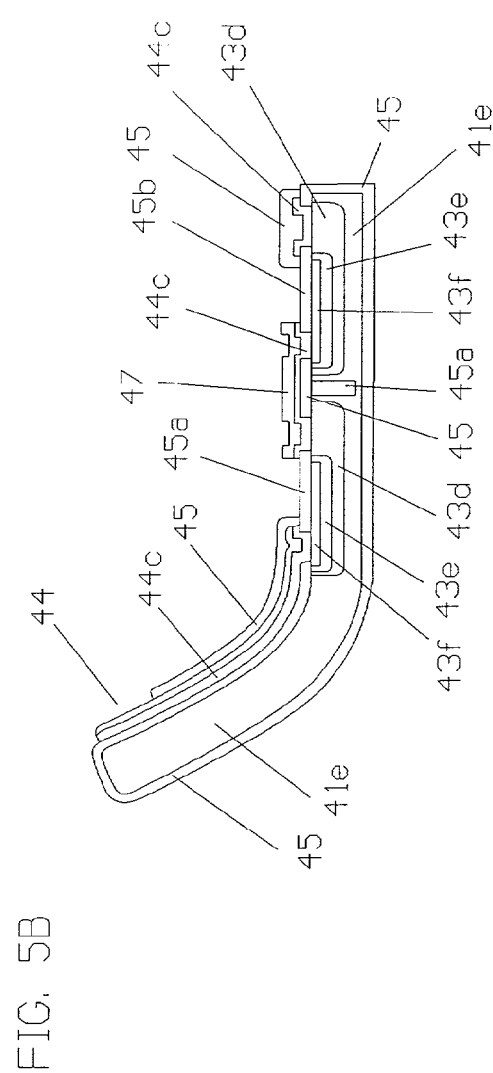

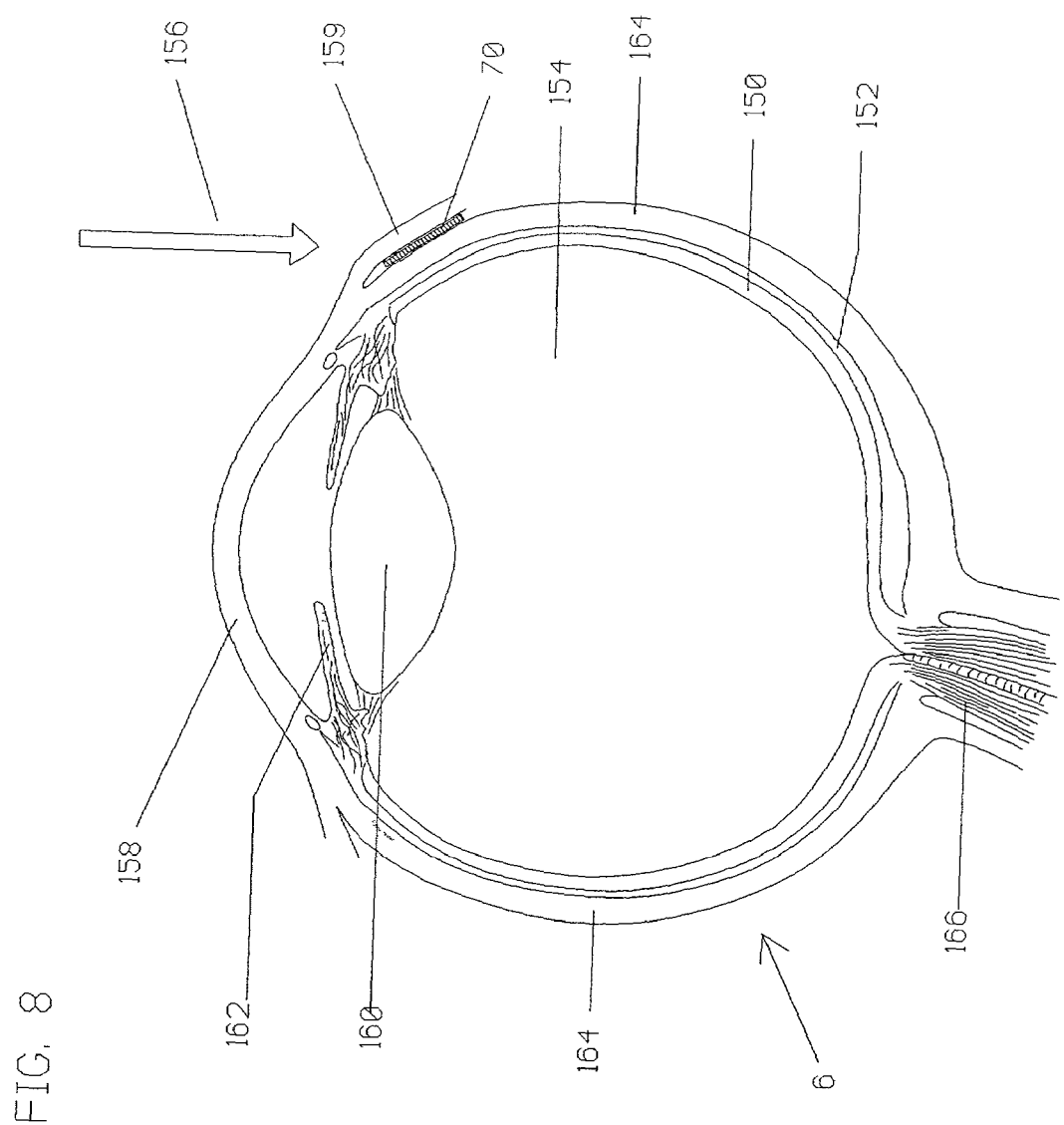

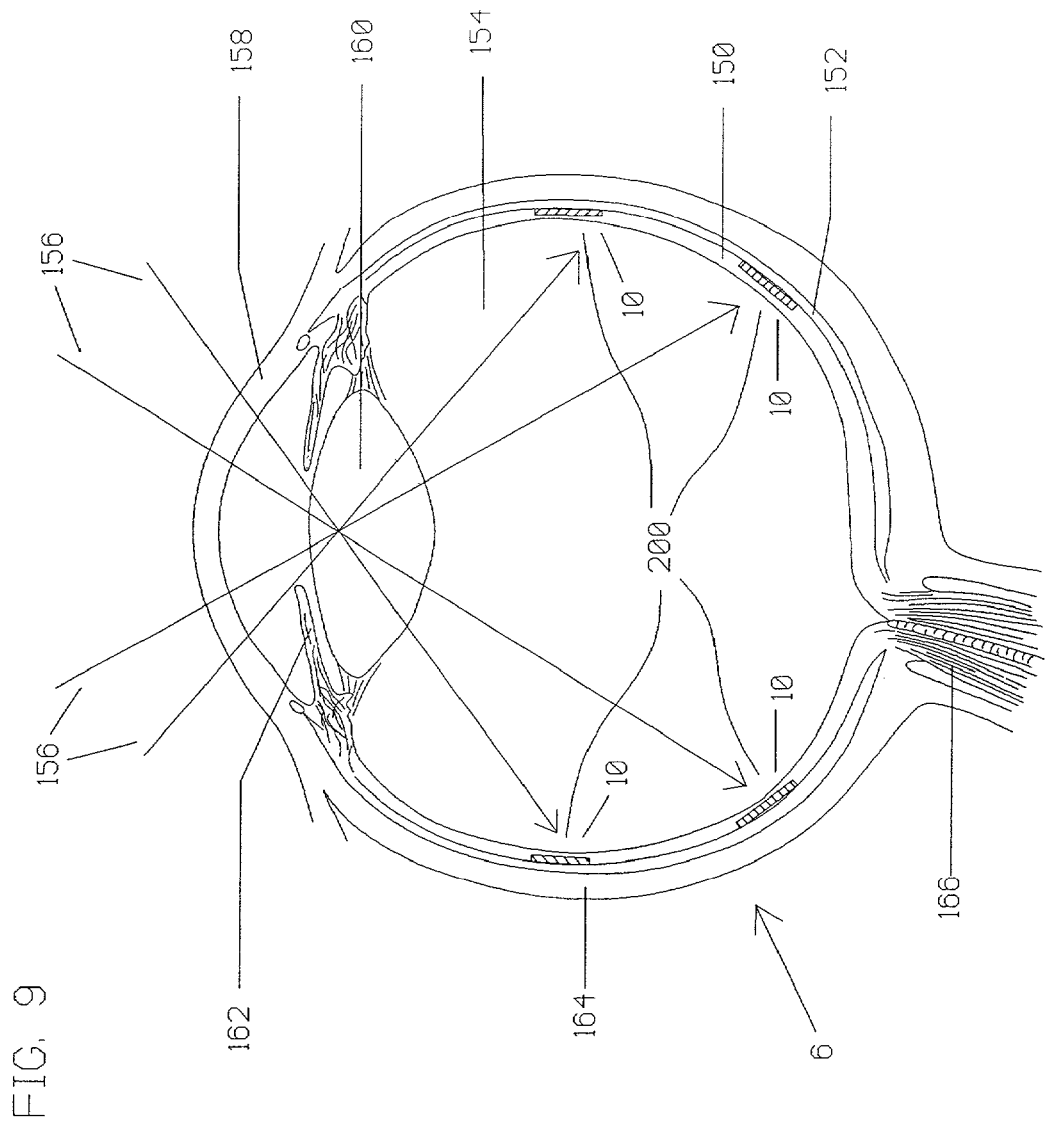

METHODS FOR IMPROVING DAMAGED RETINAL CELL FUNCTION

This application claims the benefit of provisional application serial no. 60/301,877, entitled "METHOD OF IMPLANTING A RETINA STIMULATION DEVICE FOR GENERALIZED RETINAL ELECTRICAL STIMULATION", filed Jun. 29, 2001, and is hereby incorporated by reference in its entirety.

FIELD OF THE INVENTION

The present invention is directed to improving retinal cell visual function in partially damaged and/or degenerated retinas and also to protecting retinal cells from degeneration.

BACKGROUND

Many human retinal diseases cause vision loss by partial to complete destruction of the vascular layers of the eye that include the choroid and choriocapillaris, both of which nourish the outer anatomical retina and a portion of the inner anatomical retina of the eye.

Many other retinal diseases cause vision loss due to partial to complete degeneration of one or both of the two anatomical retinal layers directly, due to inherent abnormalities of these layers. The components of the retinal layers include Bruch's membrane and retinal pigment epithelium which comprise the "outer anatomical retinal layer", and the photoreceptor, outer nuclear, outer plexiform, inner nuclear, inner plexiform, amacrine cell, ganglion cell and nerve fiber layers which comprise the "inner anatomical retinal layer", also known as the "neuroretina". The outer portion of the neuroretina is comprised of the photoreceptor and bipolar cell layers and is also known as the "outer retina" which is to be distinguished from the "outer anatomical retinal layer" as defined above. Loss of function of the outer retina is commonly the result of dysfunction of the outer anatomical retinal layer that provides nourishment to the outer retina and/or to direct defects of the outer retina itself. The final common result, however, is dysfunction of the outer retina that contains the light sensing cells, the photoreceptors. Some of these "outer retina" diseases include age-related macula degeneration, retinitis pigmentosa, choroidal disease, long-term retinal detachment, diabetic retinopathies, Stargardt's disease, choroideremia, Best's disease, and rupture of the choroid. The inner portion of the neuroretina, however, often remains functionally and anatomically quite intact and may be activated by the appropriate stimuli.

While researchers have reported efforts to restore visual function in humans by transplanting a variety of retinal cells and retinal layers from donors to the subretinal space of recipients, no sustained visual improvement in such recipients has been widely accepted by the medical community.

Multiple methods and devices to produce prosthetic artificial vision based on patterned electrical stimulation of the neuroretina in contact with, or in close proximity to, the source of electrical stimulation are known. These devices typically employ arrays of stimulating electrodes powered by photodiodes or microphotodiodes disposed on the epiretinal side (the surface of the retina facing the vitreous cavity) or the subretinal side (the underneath side) of the neuroretina. Such methods and implantable prosthetic electrical devices, designed to replace missing and damaged cells, are used to partially treat blindness in which the outer retinal cells have degenerated, but where the inner retinal layer is at least partially intact. Known devices typically employ arrays of stimulating electrodes powered by photodiodes or microphotodiodes (components that produce an electrical current or voltage potential in response to light) disposed on the epiretinal side or the subretinal side of the neuroretina. These devices can improve light perception. For example, subretinal implantation at discrete retinal locations has been shown to mimic light perception-mediated signaling; in one study (Chow and Chow, 1997), electrodes powered by external photodiodes were implanted in the subretinal space of adult rabbits. When the photodiodes, but not the rabbits' eyes themselves, were exposed to a flash of light, signaling in the brain visual cortex resembled that induced by light stimulation of the eyes. Further animal studies have demonstrated the safety and efficacy of such devices (Peachey and Chow, 1999).

Examples of devices designed to be implanted predominantly subretinally include "Surface Electrode Microphotodiodes" (SEMCPs) (Chow, U.S. Pat. No. 5,024,223, 1991), Independent Surface Electrode Microphotodiodes (ISEMCPs and ISEMCP-Cs) (Chow and Chow, U.S. Pat. No. 5,397,350, 1995; Chow and Chow, U.S. Pat. No. 5,556,423, 1996), multi-phasic microphotodiode retinal implants (MMRIs, such as MMRI-4) (Chow and Chow, U.S. Pat. No. 5,895,415, 1999), and VGMMRIs (Chow and Chow, U.S. application Ser. No.09/539,399, 2000). All these devices can be generically called Silicon Retinal Prostheses (SRP). MMRIs and VGMMRIs are designed to be used by themselves alone, or with an externally worn adaptive imaging retinal stimulation system (AIRES). These implants effectively improve perception of light and dark.

Cellular electrical signals also play important developmental roles, enabling nerve cells to develop and function properly. For example, nerve cells undergo constant remodeling, or "arborization", during development related to electric signaling. First an extensive preliminary network is formed that is then "pruned" and refined by mechanisms that include cell death, selective growth, loss of neurites (axonal and dendritic outgrowths), and the stabilization and elimination of synapses (Neely and Nicholls, 1995). If a neuron fails to exhibit or is inhibited from transducing normal electrical activity during arborization, axons fail to retract branches that had grown to inappropriate positions.

The application of electric currents to organ systems other than the eye is known to promote and maintain certain cellular functions, including bone growth, spinal cord growth and cochlear spiral ganglion cell preservation (Acheson et al., 1991; Dooley et al., 1978; Evans et al., 2001; Kane, 1988; Koyama et al., 1997; Lagey et al., 1986; Leake et al., 1991; Leake et al., 1999; Politis and Zanakis, 1988a; Politis and Zanakis, 1988b; Politis and Zanakis, 1989; Politis et al., 1988a; Politis et al., 1988b).

In other studies, the application of growth and neurotrophic-type factors was found to promote and maintain certain retinal cellular functions. For example, brain-derived neurotrophic factor (BDNF), neurotrophin-4 (NT-4), neurotrophin-5 (NT-5), fibroblastic growth factor (FGF) and glial cell line-derived neurotrophic factor (GDNF) have been shown to enhanced neurite outgrowth of retinal ganglion cells and to increase their survival in cell culture. GDNF has been shown to preserve rod photoreceptors in the rd/rd mouse, an animal model of retinal degeneration. Nerve growth factor (NGF) injected into the intra-ocular area of the C3H mouse, also a model of retinal degeneration, results in a significant increase of surviving photoreceptor cells compared to controls (Bosco and Linden, 1999; Caleo et al., 1999; Carmignoto et al., 1989; Cui et al., 1998; Frasson et al., 1999; Lambiase and Aloe, 1996; Reh et al., 1996). No methods or devices, however, to improve the general inherent visual function of damaged retinal cells distant from a source of electrical stimulation through the use of chronic electrical stimulation applied to the neuroretina from either within the eye or in direct contact with the outside of the eye are known. Also unknown is the application of growth or neurotrophic-type factors to further improve the ability of an electrical retina prosthesis that applies chronic electrical stimulation to the eye to improve retinal visual function.

SUMMARY

In one aspect, the invention provides a method of improving visual function that includes the perception of brightness in the presence of light, the perception of darkness in the absence of light, the perceptions of contrast, color, resolution, shape, motion, and visual field size of a damaged retina in a human eye by applying electrical stimulation to the damaged retina, eye or to both with a source of electrical stimulation wherein this electrical stimulation improves visual function of at least a portion of the damaged retina not in contact with the source of electrical stimulation.

In another aspect, the invention provides methods of treating primary and secondary visual degradation resulting from a damaged retina by applying electrical stimulation to the eye with the damaged retina with a source of electrical stimulation, wherein a portion of the damaged retina not in contact with the source of electrical stimulation is treated. The damaged retina, for example, may comprise damaged photoreceptor cells, and such cells peripheral to the source of electrical stimulation exhibit improved visual function as a result of the electrical stimulation.

Both of these aspects of the invention may have the following characteristics. Conditions that result in damaged retinas that may be treated with the various embodiments of the invention include age-related macular degeneration, retinitis pigmentosa, long-term retinal detachment, diabetic retinopathies, Stargardt's retinopathy, Leber's congenital amaurosis, Best's Disease, and choroidal disease or damage. Electrical stimulation may be, for example, provided to the retina or eye. Electrical sources include, e.g., a device or devices that contacts the eye or retina; when electrical stimulation is provided via this device or devices, at least a portion of the damaged retina distant, peripheral (or both) to the portion of the retina in contact with the device exhibits improved visual function. Suitable devices that provide electrical stimulation may have at least one photoactive surface (having one or more photodiodes) that is electrically connected to at least one stimulating electrode. Useful devices include Retinal Stimulation Devices (RSDs) comprising at least one of each: substrate, photoconductive/photovoltaic photodetector, such as a photodiode and/or related devices, stimulating electrode, and ground return electrode. RSDs may further comprise an electrical ground and an insulated conductor and a silicon tail. The substrate may also be fenestrated. The stimulating electrode of an RSD may be, for example, an anode or a cathode; the ground return electrode comprising an opposite polarity of the stimulating electrode. Examples of RSDs include ISEMCPs, ISEMCP-Cs and MMRIs. Electrical stimulation may be applied in response to light or may be applied intermittently in concert with or independently of light. The device may also comprise an inductive receiver and/or a solar cell, and/or a battery. The device may also comprise at least one electrode placed in contact with any portion of the eye and electrically connected to a source of stimulating current. Suitable locations of the eye for stimulation include, but are not limited to, the subretinal space, the epiretinal space, the subscleral space, the subconjunctival space, the vitreous cavity and the anterior chamber. Useful voltage potentials ($V_p$'s) of electrical stimulation are $-20V \leq V_p \leq +20V$.

In a further aspect, the invention provides a method of improving visual function in a damaged macula of a human eye by first selecting at least one device that is configured to generate an electrical current in response to light exposure; the device having at least one pixel; and implanting this device (or devices) in the subretinal space in a position that is peripheral to the macula.

In another aspect, the invention provides a method of improving visual function by implanting a device in an eye of a patient having an outer neuroretina disease (such as age-related macular degeneration, retinitis pigmentosa, long-term retinal detachment, diabetic retinopathies, Stargardt's retinopathy, Leber's congenital amaurosis, Best's Disease or choroidal disease or injury), the method comprising selecting at least one device configured to generate an electrical current in response to exposure to a source of light, each of the at least one devices comprising at least one pixel; and implanting the device in a subretinal space in an eye of the patient having the outer retina disease, wherein the device is positioned in one of a peripheral and mid-peripheral region in the subretinal space outside of a macula of the eye. The device or devices may be implanted at a position in the subretinal space between about a 5° and an 80° angle off-axis from the macula, wherein the angle is defined by an intersection of an axis line extending from the macula to a central portion of the pupil and an off-axis line extending from the device to the central portion of the pupil. The device or devices may be implanted in any region of the retina, e.g. the temporal and/or nasal half retina region of the eye, or symmetrically around a region centered by the macula.

In another aspect, the invention provides methods of implanting a device in a human eye, the method comprising implanting at least one device in one of a peripheral and mid-peripheral region in the subretinal space outside of the macula, wherein the device(s) is configured to generate an electrical current in response to exposure to a source of light, the device(s) comprising at least one pixel, and wherein the device is positioned away from a region of damaged retinal cells.

In all aspects of the invention, the devices used in these methods to improve visual function of a damaged retina may be surgically implanted into the subretinal space at an angle between about 5° and 80° off-axis from a macula, wherein the angle is defined by an intersection of an axis line extending from the macula to a central portion of a pupil, and an off-axis line extending from the device to the central portion of the pupil. The device (with or without at least one fenestration) may be surgically implanted in at least one sector of a retina, excluding the macula. The device or devices may be implanted in the temporal or nasal (or both) half retina region of the eye, or symmetrically around a region centered by the macula.

BRIEF DESCRIPTION OF THE DRAWINGS

FIG. 2A is a plan view of a preferred embodiment of RSD, showing the general plan structure of RSDs.

FIG. 2B is a section view of a preferred embodiment of this invention at I—I of FIG. 2A showing the general sectional structure of RSDs.

FIG. 2C is a section view showing the placement of a RSD of FIGS. 2A and 2B in the subretinal space of the eye.

FIG. 3A is a plan view of another preferred embodiment of the RSD showing the silicon tail of the RSD that contains the ground return electrode.

FIG. 3B is a sectional view of the preferred embodiment of the RSD of this invention at II—II of FIG. 3A. The inset is a magnified portion of FIG. 3B.

FIGS. 4A and 4B are plan and sectional views respectively of yet another preferred embodiment of a RSD showing at least two photodiodes electrically connected in series on the RSD to increase the voltage and resultant current output of the device. The sectional view 4B is through III—III of the plan view 4A.

FIGS. 5A and 5B are plan and sectional views respectively of yet another preferred embodiment of a RSD showing an Opsistor photodiode electrical configuration in the RSD to allow biphasic stimulating currents to be produced that are modulated by different wavelengths of light. The sectional view 5B is through IV—IV of the plan view 5A.

FIG. 8 is a cross-sectional view of yet another embodiment of this invention showing the RSD of FIGS. 2A and 2B where the RSD is implanted between the conjunctiva and the scleral surface.

FIG. 9 is a cross-sectional view of an embodiment showing an array of retina stimulation devices positioned in an eye in the periphery and/or mid-periphery outside the macula.

DETAILED DESCRIPTION OF THE PRESENTLY PREFERRED EMBODIMENTS

Figure 1A:
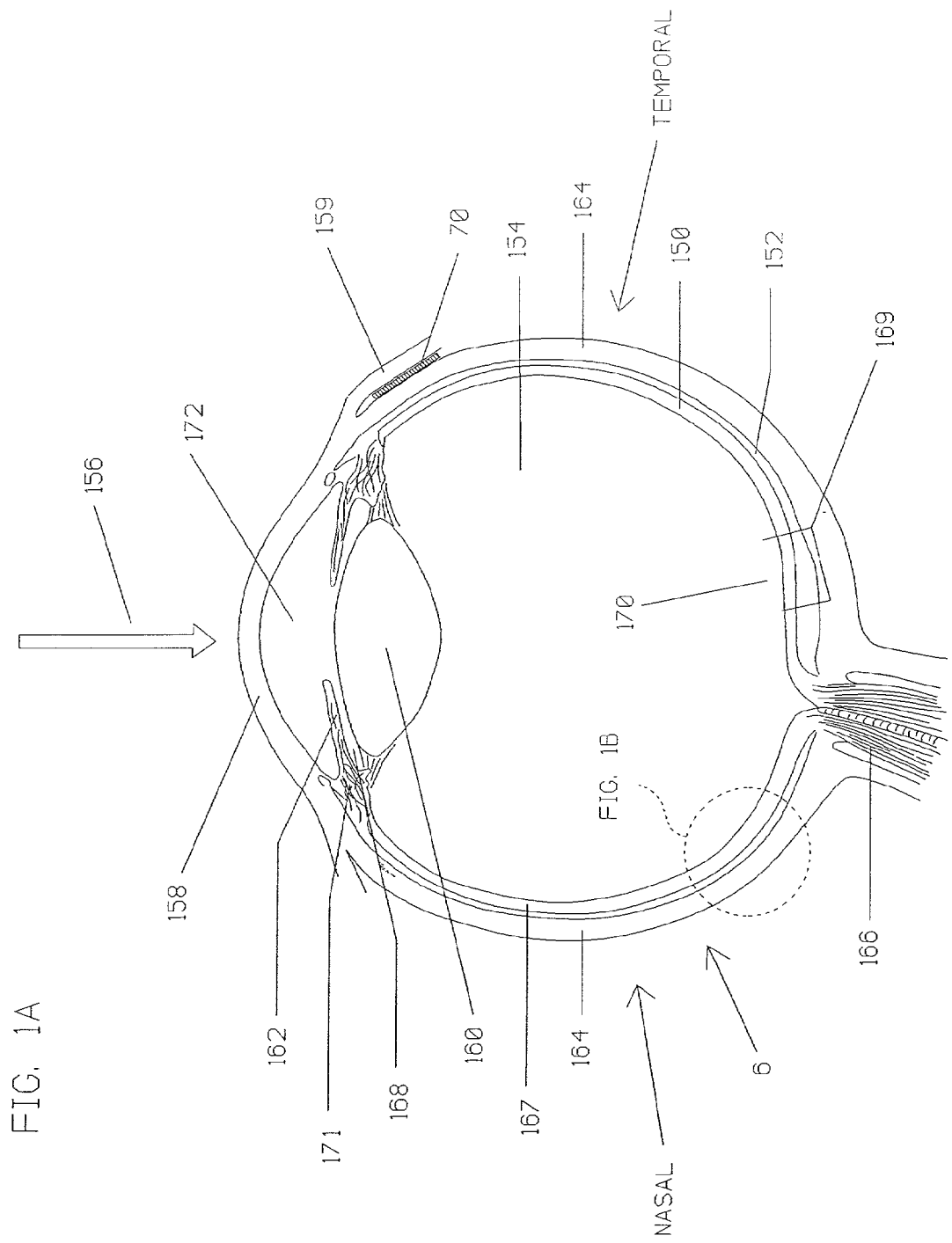
FIG. 1A presents top cross-section of a human eye.

In the course of testing for the safety and efficacy of retinal implants in humans blinded by retinitis pigmentosa, an unexpected and surprising observation was made: even though the implants were placed at a discrete location in the subretinal space (acting as a prosthesis), vision was improved not only in those discrete locations as expected, but also in distant locations of the retina. Thus chronic electrical stimulation in specific locations enhanced retinal cell function throughout the eye. This "halo effect" can be used to improve vision in those individuals who suffer from diseases, conditions and traumas that have damaged the outer retinal layer but leave the inner retinal layer at least partially intact. Although prosthetic electrical devices designed to replace damaged or missing retinal cells have been used to treat vision loss caused by outer retinal degeneration, electrical stimulation to improve large areas of retinal cell visual function is novel. As a non-limiting explanation, the promotion of improved retinal cell visual function by chronic electrical stimulation may be explained by the stimulation of production and release of growth factors; more specifically, neurotrophic-type growth factors, by the stimulated retinas. The synthesis and/or secretion of neurotrophic factors would then improve retinal cell function and survival in conditions where these activities would be lost.

The present invention discloses both devices and novel methods to electrically stimulate the retina to improve large areas of retinal visual function and to protect the retina from degeneration.

Definitions

Subject/patient

A subject (patient) may be a human being or a non-human animal, but is preferably a human. Usually the individual has suffered some type of retinal damage and/or degeneration that results in some degree of visual loss and/or has a condition that will result in retinal damage and/or degeneration. A normal (healthy) subject does not have a condition that will result in retinal damage and/or degeneration and/or has not suffered retinal damage and/or degeneration.

Improving Visual Function

Improving visual function refers to improving a targeted function of the eye, selected by the artisan, and includes improving any to all of the following capabilities of the eye, retina and visual system: perception of brightness in the presence of light, perception of darkness in the absence of light, perceptions of contrast, color, shape, resolution, movement and visual field size.

Primary visual degradation means loss of visual function due to malfunctioning, damaged or degeneration of structures found in the eye. Secondary visual degradation means loss of visual function due to secondary damage, typically from lack of use of the vision-associated portions of the brain. Improving visual function means to improve the visual function of primary visual degradation, secondary visual degradation or both.

Eye/eyeball

The eye (or eyeball) has the usual definition in the art. Eye includes all interior and exterior surfaces, components, contents and cavities of the eye. The eye does not include the eyelid.

The retina of the eye can be divided into sectors as is commonly accepted in the art. Such sectors are described by the use of the terms temporal, nasal, superior, inferior, by clock hour designation, and by the number of degrees away from the macula. For example, the temporal sector of the retina is the retina temporal to a perpendicular plane cutting through retina from the 12 o'clock to the 6 o'clock positions and through the macula. In another example, the superior sector is the retina superior to a perpendicular plane cutting through the 9 o'clock to 3 o'clock positions and through the macula. In a further example, the superior-temporal sector is the intersection of these two sectors, a pie-shaped area delineated from the 9 o'clock position of the peripheral retina to the macula and then clockwise to the 12 o'clock position. More specific locations of the retina can be designated by degrees away from the macula and clock hour location: for example, 20 degrees away from the macula at the 3 o'clock (nasal) position. The number of degrees away from the macula is in visual axes degrees. These axes all intersect through the lens of the eye.

The visual field sectors correspond oppositely to the retinal sectors as is commonly understood in the art. For example, the superior-temporal sector of the retina corresponds to the inferior-nasal portion of the visual field.

Peripheral

To be peripheral to an object, device or other landmark includes all surrounding parts, but not the object, device or landmark, i.e., the object, device or landmark, together with the peripheral portion, constitutes the whole.

Light

Light refers not only to the electromagnetic spectrum that humans can readily perceive visually (approximately 400 nm to 750 nm), but also includes ultraviolet light (<400 nm in wavelength) as well as infrared light (>750 nm in wavelength).

Indications

The invention can be used to improve visual function in subjects in which the retina is damaged by disease, degeneration, condition, or trauma and/or to slow down or stop the progression of damage by disease, degeneration, condition or trauma. Common diseases, conditions, degeneration or trauma that are particularly amenable to this treatment include age-related macula degeneration, retinitis pigmentosa, Leber's congenital amaurosis, Stargardt's disease, Best's disease, diabetic retinopathy, long-term retinal detachment, and choroidal damage.

Eye structure

Referring to the drawings, FIG. 1A illustrates a section through the eyeball. The neuroretina 150 comprises multiple layers of cells and structures (see FIG. 1B). The photoreceptor components of the retina are situated within the neuroretina which covers the internal posterior cavity of the eye, terminating anteriorly at the ora serrata 167. The ciliary body 168 and the iris 162 are covered by extensions of the retina, lacking photoreceptor components. The outermost layers of the eye consist of the sclera 164 and cornea 158. The sclera is pierced by the emerging optic nerve 166. The lens 160 and vitreous cavity 154 are also indicated. The macula 169 of the retina is typically a 3 mm by 5 mm oval region, at the center of which is the fovea 170.

Figure 1B:
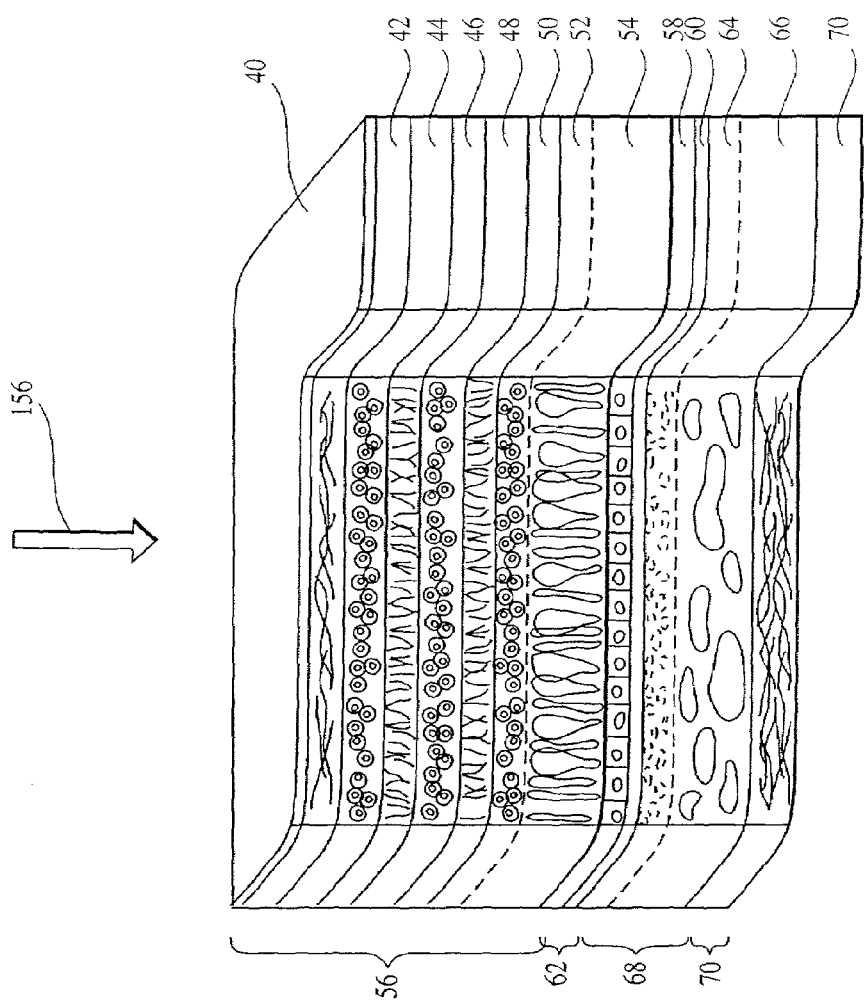
FIG. 1B presents a cross-section through the human eye that include the layers of the outer and inner anatomical retina, as indicated by the inset of FIG. 1A.

The layers of the eye at the posterior pole from inside to outside are shown in FIG. 1B: internal limiting membrane 40, nerve fiber layer 42, ganglion and amacrine cell layer 44, inner plexiform 46, inner nuclear layer 48, outer plexiform 50, outer nuclear and bipolar cell layer 52, and photoreceptor layer 54, all of which constitute the anatomical inner retinal layer, also known as the neuroretina 56. The retinal pigment epithelium 58, and Bruch's membrane 60 constitute the outer retinal layer 62. The choriocapillaris 64, and choroid 66 comprise the choroidal vasculature 68. The outer coat of the eye is the sclera 70. Light 156 enters the retina as shown.

Devices

Any device that provides (or can apply) electrical stimulation, diffuse or discrete, to the eye can be used as a source of electrical stimulation. Preferably, these devices are retina stimulation devices (RSDs); more preferably, the RSDs are powered by incident light, ambient and/or amplified, although other means, such as batteries, external solar cells, supplied electrical current or potential voltage, may also be used. Such external power may be provided to the RSDs via direct electrical conductor and/or by electromagnetic power such as but not limited to radio frequency signals and light. The RSDs may be supplied such external power in a pattern such as cyclically, and/or in complex waveform patterns. Such external power provided to the RSDs may also be activated and deactivated by a user at will, which may be desirable when a user is sleeping. One or a plurality of devices may be used to apply electrical stimulation.

A variety of electrical devices have been described (Chow, U.S. Pat. No. 5,024,223, 1991; Chow and Chow, U.S. Pat. No. 5,397,350, 1995; Chow and Chow, U.S. Pat. No. 5,556,423, 1996; Chow and Chow, 1997; Chow et al., 2001; Chow and Peachey, 1999; Chow and Chow, U.S. Pat. No. 5,895,415, 1999; Chow and Chow, U.S. Pat. No. 6,230,057 B1, 2001), and are hereby incorporated by reference.

The RSD is preferably a disk-shaped silicon chip device, approximately 2 mm in diameter and 25 µm in thickness, comprising one or more groups of one or more photodiodes electrically connected in series, having one or more stimulating electrodes and one or more ground return electrodes. The RSD can be flexible or rigid and may be designed to conform to the structural curvature of the outside or inside of the eye, the subretinal space, the epiretinal surface, and/or the subscleral space. Also, the RSD may consist of multiple electrically isolated subunits connected by a flexible mesh. RSDs may be fabricated to function suitably with diameters that vary from 0.005 to 25 mm, and thicknesses that vary from 0.2 µm to 1000 µm, although those skilled in the art will appreciate that dimensions falling outside of the aforementioned values may also be suitable. The stimulating electrode or electrodes contacting the epiretinal or the subretinal side of the neuroretina may be the anode or cathode with the ground return electrode being the opposite polarity of the stimulating electrode. If the electrodes are on the eye surface, the stimulating electrode or electrodes contacting the outside of the eye may also be the anode or the cathode with the ground return electrode being the opposite polarity of the stimulating electrode.

In a preferred embodiment, the silicon chip RSD is a single photodiode 2 mm diameter and 25 µm thick with its photoactive surface facing incident light and its retinal stimulating electrode disposed on the same surface and electrically connected to the photodiode. On the opposite surface of the RSD is an electrode electrically connected to the photodiode that serves as the ground return electrode for the RSD. In use, the RSD silicon chip is preferably implanted surgically into the subretinal space of an eye in a paracentral location relative to the macula (i.e., peripheral to the macula). In this embodiment, it is preferred that the retinal stimulating electrode on the photoactive surface of the RSD photodiode is in contact with the inner retina from the subretinal space and is facing incident light, and the electrode is a cathode. Diffuse electric currents developed by the cathode, when the RSD is exposed to light, stimulate the neuroretina above, surrounding, and at a distance from the RSD to improve the damaged retina's inherent visual function. Such visual function improvement has been observed in a clinical study involving multiple patients implanted with such devices, resulting from chronic subretinal electrical stimulation produced by an implanted, high pixel density, artificial silicon retina device. However, it is recognized that a high pixel density of a retina stimulator is not necessary to achieve a general electrical stimulation of the retina. If needed, more than one RSD is implanted in an eye to stimulate a larger area of retina, and multiple RSDs would preferably be implanted in paracentral locations relative to the macula such as one in each of the four paracentral quadrants, approximately, but not limited to, 5 to 80 degrees peripheral to the macula.

In another preferred embodiment, the electrical ground of the RSD is brought into the vitreous cavity via an insulated conductor preferably fabricated on a silicon tail that is part of the RSD with an exposed ground return electrode at the end of the conductor on the tail. This configuration directs the electrical current flow more efficiently between the stimulating and ground return electrodes of the RSD into a more through-the-retina, transretinal route and also through a smaller area of the neuroretina compared to the first RSD embodiment without this tail configuration. A modification of this preferred embodiment extends the tail into the lens capsule of the eye where it terminates in a photodiode array connected in series and/or parallel with the main RSD to provide additional voltage and/or current to stimulate the neuroretina. The purpose of placing the photodiode array in the lens capsule is to allow the photodiode array to be exposed to brighter intensities of incident light. In this modification of the preferred embodiment, the ground return electrode is located on the photodiode array placed in the lens capsule.

In yet another preferred embodiment, at least two photodiodes are fabricated on the RSD that are electrically connected in series to produce higher voltages and higher resultant currents than is possible without such series connections. The RSD is fabricated in versions where the ground return electrode is located either in the subretinal space, or in the vitreous cavity at the end of a silicon tail (Chow and Chow, U.S. application Ser. No. 09/539,399).

In yet another preferred embodiment, at least two photodiodes are fabricated on a RSD and electrically connected in a reverse parallel manner such as in an Opsistor fashion (Chow and Chow, U.S. Pat. No. 5,837,995, 1998) to provide biphasic and variable levels of stimulating electric currents both controlled by the use of different wavelengths of external visible and/or infrared light.

In yet another preferred embodiment, fenestrations are fabricated into any of the aforementioned preferred embodiments of the RSD. The fenestrations allow nourishment and oxygen to flow beneficially from the choroidal circulation and the outer anatomical retina into the inner anatomical retina for RSDs placed in the subretinal space.

With regard to FIG. 1B, when an RSD 10 is inserted in the subretinal layer, it is inserted within the retina between the inner retinal layer 56 (that may or may not contain a functional photoreceptor layer 54) and the outer retinal layer 62, in the potential space zone 72. The overlying inner retinal layer consisting of photoreceptors and their cell bodies 54, 52, bipolar cells 48 and horizontal cells 52 are also shown. The bipolar cells 48 and ganglion cells 44 are in the innermost area of the inner retinal layer, processing visual cues such as electric signals for distant transmission through the optic nerve to the brain.

Referring to the drawings, as shown in FIGS. 2A and 2B, a preferred embodiment of the RSD 10 will serve as an example. In this embodiment, the RSD has a stimulating electrode side 12 and a ground return electrode side 16. The RSD is fabricated on a single thin silicon chip substrate 11 and is implanted into the subretinal space. The stimulating electrode side 12 includes at least one stimulating electrode 14a and the ground return electrode side 16 includes at least one ground return electrode 14b. Electric current is produced by the RSD photodiode photodetector 18 but may be provided by other and external current sources, such as a connected external power supply to the photodiode photodetector. In the presence of such external current sources, the photodiode would also act in a photoconductor mode.

In the embodiment of FIGS. 2A and 2B, the stimulating electrode 14a contacts the neuroretina from the subretinal space. The ground return electrode 14b contacts the retinal pigment epithelium or the remnant of this structure also from the subretinal space. Also as shown in FIGS. 2A and 2B, exemplary components of the preferred embodiment of RSD 10 include the thin P silicon substrate 11, an iridium/iridium oxide stimulating electrode 14a, a titanium adhesion layer 15a, the N+ layer 16a, the intrinsic layer 17, the P+ layer 16b, the titanium adhesion layer 15b for the iridium/iridium oxide ground return electrode 14b. Although the embodiment as described is that of a NIP (negative-intrinsic-positive construction) device, those skilled in the art will be able to readily fabricate a PIN (positive-intrinsic-negative construction) device based on the aforementioned description that is also suitable for retinal stimulation. The photodiode 18 or other electrical source preferably provides stimulation to the neuroretina from the subretinal side of the eye. Alternatively, the electrical source for stimulation could be provided from outside the eye. For example, an electrical voltage/current source such as a programmed DC or AC power supply-could send voltage and current via hardwiring to an electrode or electrodes in the subretinal space or even into the vitreous cavity of the eye. In another embodiment, a power source could transmit a signal in a wireless fashion into the eye using, for example, radio frequency (RF) telemetry systems to send signals to a coil located in the eye that communicates with the stimulation and ground electrodes that convert the RF signal into electric current. In further embodiments, a power source external to the eye (e.g. a battery and current management electronics) may be used to deliver an electrical signal to at least one electrode of a retina stimulation device implanted into a subretinal space outside of the macula. The external power source may supply the electrical signal to the RSD electrode in a wired or wireless manner, and the electrical signal can be related or unrelated to incident light. It will be obvious to those skilled in the art that other common mechanisms are also available for providing electrical energy into the eye to beneficially stimulate the retina.

FIG. 2C is a cross-sectional view showing a preferred embodiment RSD 10 of FIGS. 2A and 2B implanted in the eye 6 in the subretinal space between the neuroretina 150 and the retinal pigment epithelium 152. Light 156 entering the eye 6 through the cornea 158 and lens 160 is focused onto the RSD 10. Electrical current is generated by the RSD and provides beneficial stimulation to the overlying neuroretina 150. For purposes of reference, other structures of the eye 6 that are shown are the iris 162, the sclera 164 and the optic nerve 166.

Referring to FIGS. 3A and 3B, another preferred RSD embodiment of this invention 20 has a stimulating electrode unit 23 and a curved ground return electrode unit 26 configured for implantation into an eye such that the retinal device 20 may be positioned completely inside the eye and stimulate opposite or substantially opposite sides of the neuroretina. The two components 23 and 26 are preferably physically fabricated on a single thin silicon chip substrate 22, but may be fabricated separately and then joined together. The stimulating electrode unit 23 includes at least one stimulating electrode 23b powered by one or more electrical sources such as a photodetector 23a or photodetectors. In this embodiment, the photodetector is implemented as a photodiode 23a.

In the embodiment of FIGS. 3A and 3B, the stimulating electrode 23b contacts the neuroretina from the subretinal side. The ground return electrode 24 is preferably disposed at or near the tip of the ground return electrode unit 26. The stimulating electrode 23b and the ground return electrode 24 are disposed on opposite sides of a neuroretina, or if the neuroretina is partially missing or damaged, then on opposite sides of the remainder of the neuroretina. In this embodiment, the stimulating electrode 23b is disposed in the subretinal space of the neuroretina and the ground return electrode 24 is disposed on the epiretinal side of the neuroretina in the vitreous cavity.

Also included with the ground return electrode unit 26 of FIGS. 3A and 3B is a silicon nitrite stress layer 27 that shapes the ground return electrode unit 26 in a generally curved shape to direct the ground return electrode unit 26 into the vitreous cavity. Although a curve directs the ground electrode unit 26 into the vitreous cavity, other shapes can be used to perform the same function, such as an angled ground electrode. The ground return electrode 24 is preferably produced of iridium/iridium oxide and includes a titanium adhesion layer 24a and a P+ tub 24b disposed under a titanium adhesion layer 24a to allow electrical contact with the P doped silicon substrate 22. The retinal device 20 also preferably includes a silicon dioxide layer 25 that insulates the stimulating electrode unit 23 and ground return electrode unit 26.

As shown in FIGS. 3A and 3B, the stimulating electrode unit 23 includes at least one photodiode 23a electrically connected to its stimulating electrode 23b. The preferred number of photodiodes 23a is one per stimulating electrode unit 23. The layers of the photodiode 23a are, for example, from the incident light surface, the iridium/iridium oxide electrode 23b, titanium adhesion layer 23c, N+ tub 23d, intrinsic layer 23e, the P doped silicon substrate 22, and the silicon dioxide insulating layer 25. Those skilled in the art will appreciate that other arrangements can be used where the stimulating electrode 23b provides electric current derived from other sources, such as an external power supply hard wired to electrode 23b. Although the described preferred embodiment is that of a NIP device, those skilled in the art will be able to readily fabricate a PIN device based on the aforementioned description that is also suitable for retinal stimulation.

Also shown in FIGS. 3A and 3B, the ground return electrode unit 26 preferably includes a positioning hole 25a that allows the retinal device 20 to be positioned surgically with instruments. The ground return electrode unit 26 in another embodiment includes notches 26a that allow a secure fit for attachments that have corresponding protrusions that fit into the notches 26a, as described in more detail below.

Figure 3C:
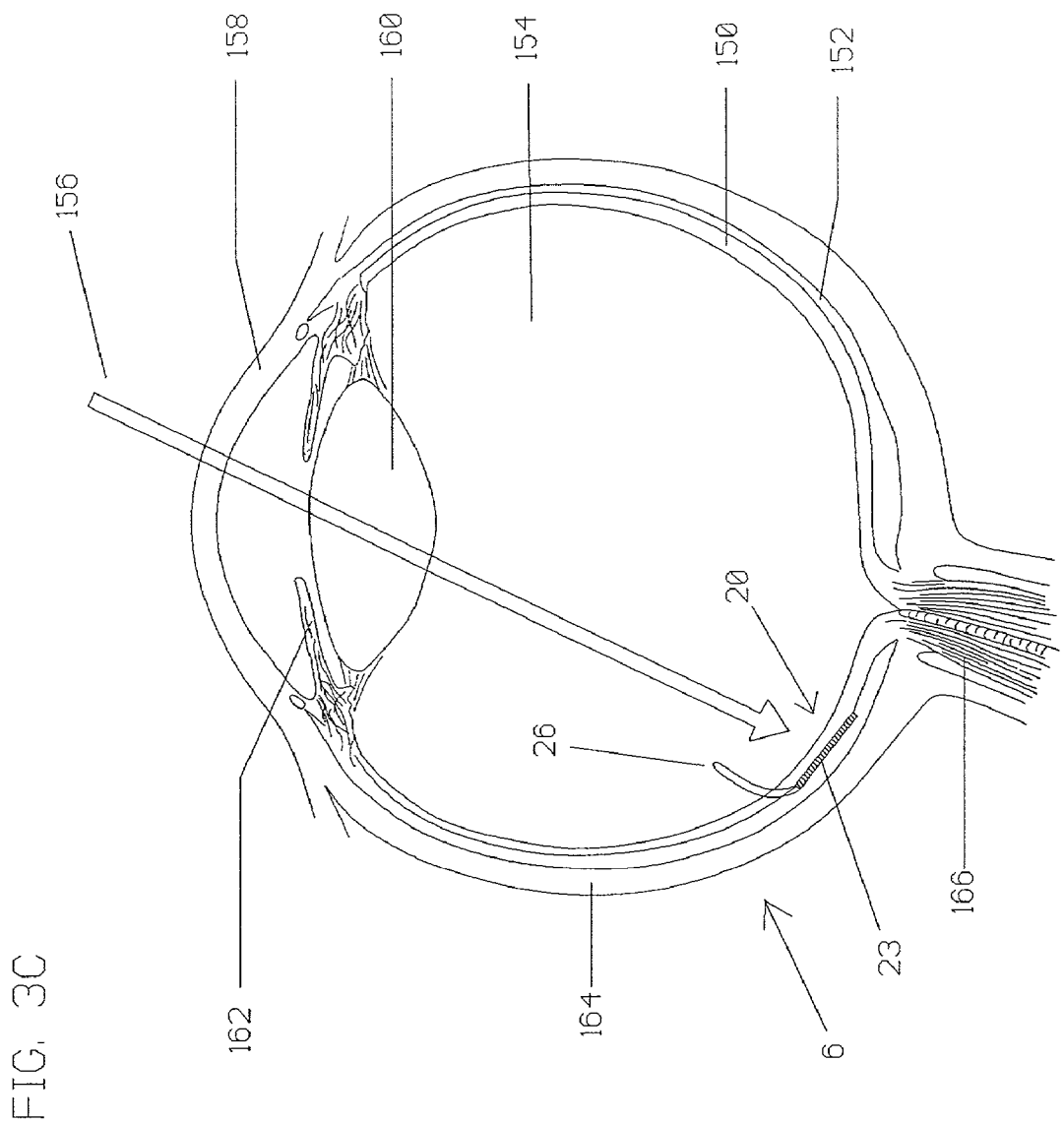
FIG. 3C is a section view showing the placement of the RSD of FIGS. 3A and 3B in the subretinal space of an eye with the silicon tail and ground return electrode in the vitreous cavity.

FIG. 3C is a cross-sectional view showing the second preferred embodiment RSD 20 of FIGS. 2A and 2B implanted in the eye 6. The stimulating electrode unit 23 is located in the subretinal space between the neuroretina 150 and the retinal pigment epithelium 152 while the ground return electrode unit 26 is located in the vitreous cavity 154. Light 156 entering the eye 6 through the cornea 158 and lens 160 is focused onto the RSD 20. Electrical current is generated by the RSD that provides beneficial stimulation to the overlying and surrounding neuroretina 150. For purposes of reference, other structures of the eye 6 that are shown are the iris 162, the sclera 164, the optic nerve 166, lens 160 and cornea 158.

Figure 3D:
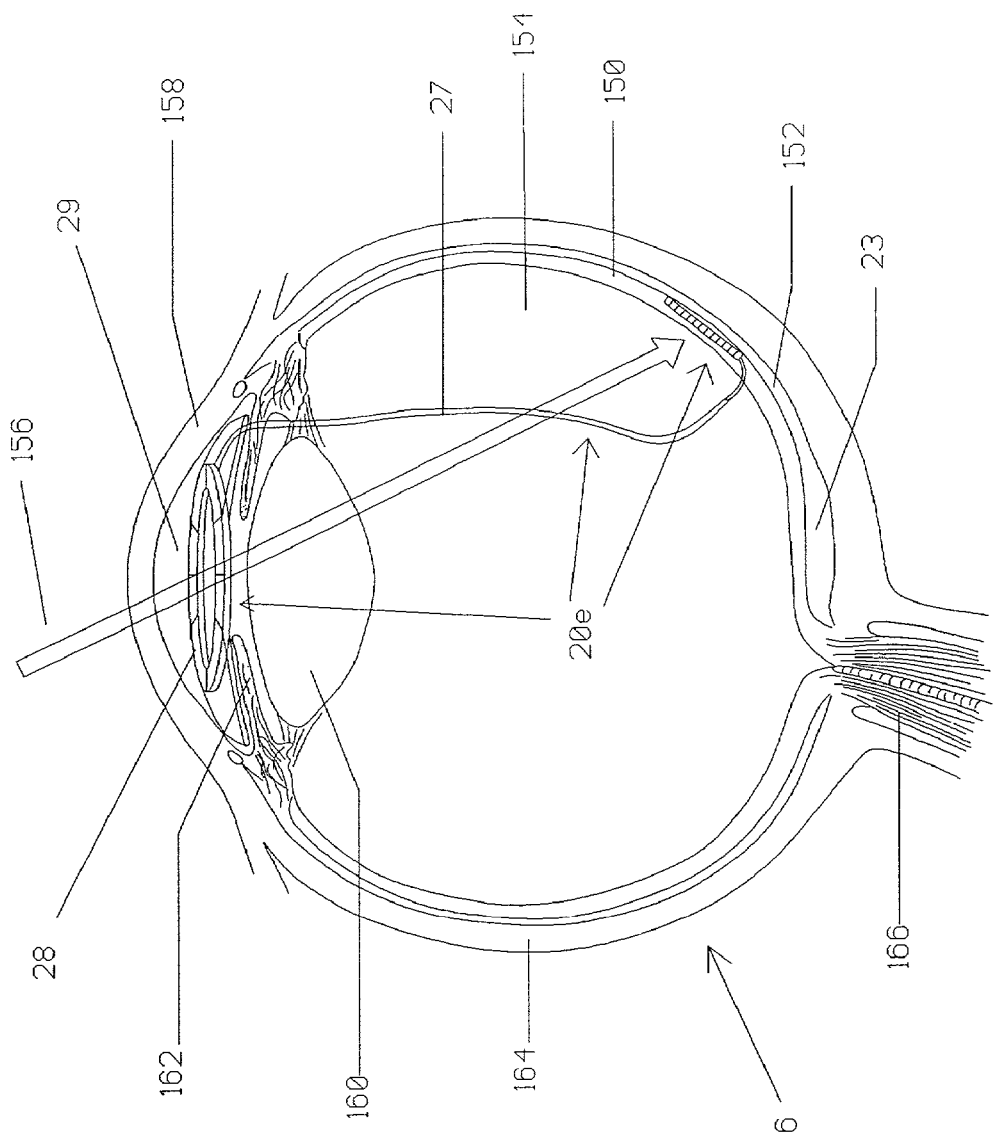
FIG. 3D is a cross-sectional view of the modified embodiment of FIGS. 3A and 3B showing the main photodiode portion of the RSD in the subretinal space and the extended tail of the RSD in the anterior chamber of the eye where it terminates in a photodiode array connected in series and/or parallel with the main photodiode of the RSD to provide additional voltage and/or current to stimulate the retina. In this latter device the ground return electrode is located on the photodiode array placed in the eye's anterior chamber.

FIG. 3D shows a cross-sectional view of a modification 20e of a preferred embodiment RSD of FIGS. 2A and 2B that includes a preferred embodiment RSD 20 as described in FIGS. 2A, 2B and 2C, and an attached tail extension 27 that electrically connects with at least one bias photodiode 28 preferably disposed in front of the iris 162 of the eye 6. The placement of at least one bias photodiode in this location allows the bias photodiode or photodiodes to be better exposed to light, compared to bias photodiodes, for example, disposed behind the iris. The bias photodiode 28 also contains the extended location of the ground return electrode 29, and the bias photodiode or photodiodes 28 provide additional voltage and/or current to the electrode stimulating unit 23 in the subretinal space. The bias photodiode or photodiodes 28 are electrically connected together in a series or parallel configuration to provide increased voltage and/or current as needed, and as is known in the art. For reference, other structures of the eye 6 that are shown are the cornea 158, lens 160, sclera 164, neuroretina 150, retinal pigment epithelium 152 and optic nerve 166, and the incident light images 156.

FIGS. 4A and 4B are plan and sectional views respectively of another embodiment of a preferred RSD showing multiple photodiodes 32 and 33 electrically connected in series on the RSD 30 to increase the voltage output of the device. The sectional view 4B is through III—III of the plan view 4A.

FIGS. 4A and 4B show the stimulating electrode unit 31 includes at least two photodiodes 32 and 33 electrically connected in series to their stimulating electrode 33b and its ground electrode 34. The ground electrode unit 36, contains a positioning hole 34a. The preferred number of photodiodes per RSD 30 is two; however, based on the design of this RSD embodiment, one ordinarily skilled in the art can readily produce a device with additional photodiodes connected electrically in series to the stimulation electrode 33b and ground return electrode 34. The layers of the photodiodes 32 and 33 are, for example, from the incident light surface, an iridium/iridium oxide stimulating electrode 33b, iridium/iridium oxide connecting straps 34c over titanium adhesion layers 33c, N+ tubs 33d, intrinsic layers 33e, the P+ layers 33f, channel stop region 35a, P silicon substrate 31e, and silicon dioxide insulating layers 35. One ordinarily skilled in the art will appreciate that other arrangements could be used where the stimulating electrode 33b provides electric current derived from other sources such as a receiving inductive coil implanted in the vitreous cavity and powered by an external transmitting inductive coil, or such as an external power supply hard wired to electrode 33b. Also, although the described preferred embodiment is that of a NIP device, a PIN device based on the aforementioned description that is also suitable for retinal stimulation.

FIGS. 5A and 5B show that the stimulating electrode unit 41 includes at least two photodiodes 42 and 43 electrically connected in a reverse parallel Opsistor fashion terminating in a stimulating electrode 47 and a ground return electrode 44. The ground return electrode unit 46, contains a positioning hole 44a. Preferably, the number of photodiodes per RSD 40 is two. However, more than two photodiodes per RSD are also contemplated. More detail on versions of these RSDs has been described (Chow and Chow, U.S. Pat. No. 5,837,995, 1998; Chow and Chow, U.S. application Ser. No. 09/564,841; Chow and Chow, U.S. application Ser. No. 09/539,399; the entirety of these references is incorporated herein by reference). The photodiodes 42 and 43 receive power from incident light, and each photodiode is powered predominantly by a different wavelength of light as determined by the light filters 45a and 45b. Preferably, one light filter 45a or 45b passes a portion of visible and/or infrared light while the other filter passes another portion of visible and/or infrared light. The structures shown are the iridium/iridium oxide stimulation electrode 47, iridium/iridium oxide ground return electrode 44, titanium adhesion layers and titanium connecting straps 44c, N+ tubs 43d, intrinsic layers 43e, P+ layers 43f, channel stop region 45a, P silicon substrate 41e, and silicon dioxide insulating layers 45. Other arrangements may be used where the stimulating electrode 47 and ground return electrode 44 provide electric current derived from another source, such as an external power supply hard wired to the electrodes 47 and 44, or such as a receiving inductive coil implanted in the vitreous cavity and powered by an external transmitting inductive coil.

Figure 6:
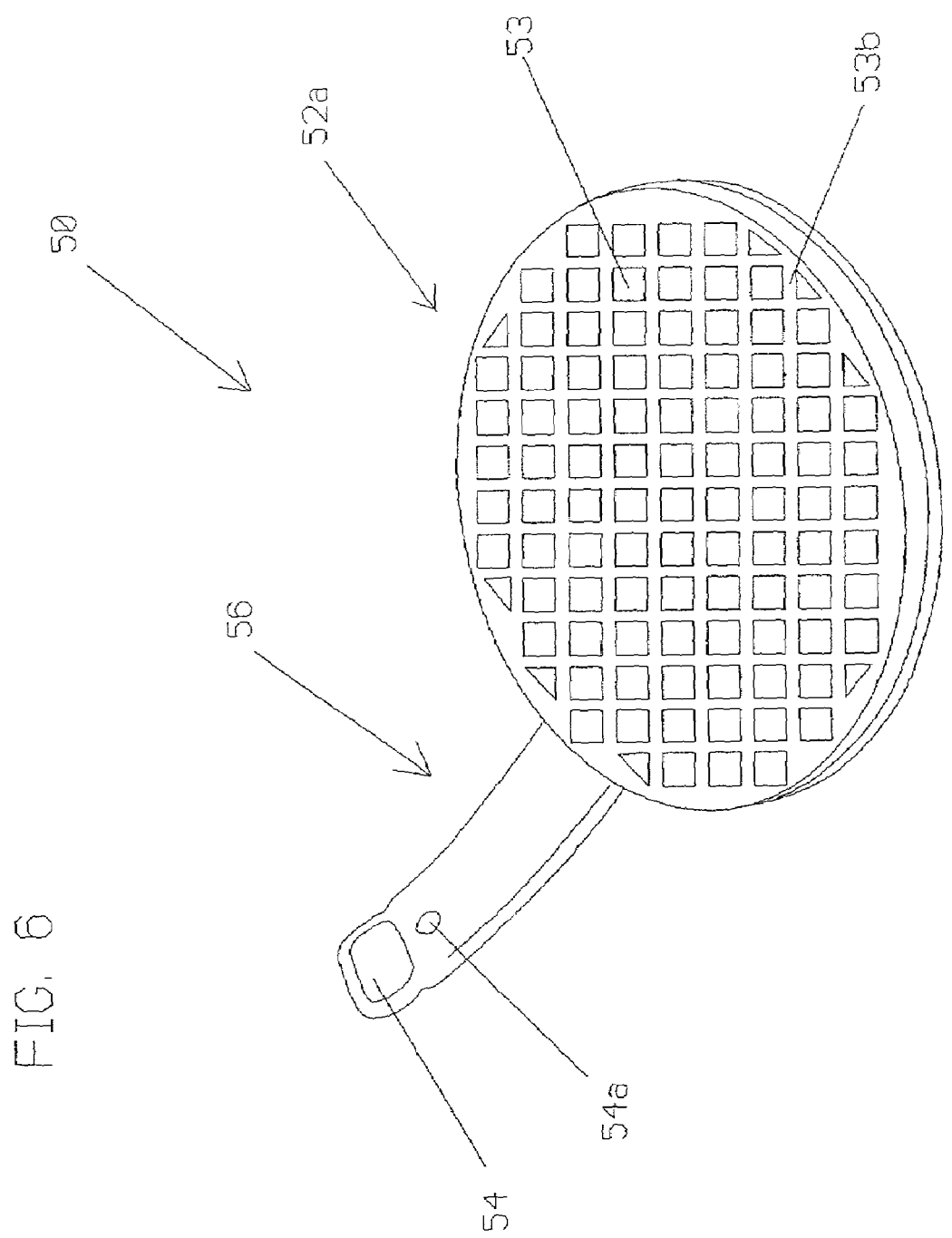
FIG. 6 is a perspective view of yet another preferred embodiment of a RSD, fabricated with fenestrations.

FIG. 6 is a perspective view of another embodiment 50 of the RSDs shown in FIGS. 2A and 2B, and 3A and 3B. The stimulation electrode unit 52a of this preferred embodiment 50 is similar to the stimulation electrode units of the preferred embodiments of FIGS. 2A and 2B, and FIGS. 3A and 3B except that the stimulation electrode unit 52a is perforated. It is fabricated as a disk-shaped silicon web to allow nourishment to flow between the choroid and the neuroretina, and it has at least one perforated electrode 53b encompassing the surface of the stimulation electrode unit 52a. The ground return electrode unit 56 is fabricated with at least one positioning hole 54a and at least one ground return electrode is 54.

Figure 7:
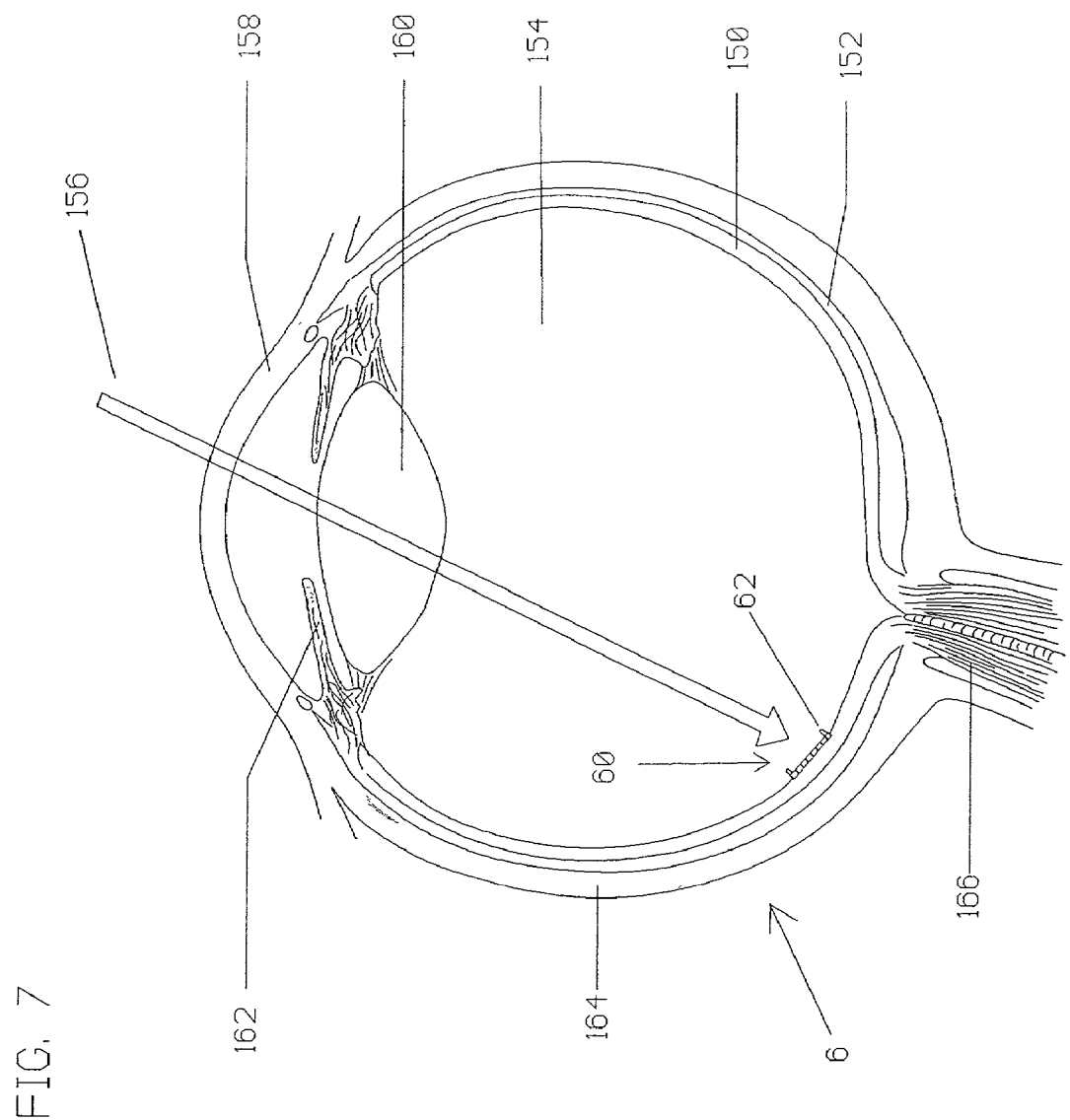
FIG. 7 is a cross-sectional view of yet another embodiment of this invention showing an RSD of FIGS. 2A and 2B where the RSD implanted on the epiretinal surface of the retina and secured to the retina by tacks.

FIG. 7 is a cross-sectional view showing another preferred RSD embodiment 60 implanted in an eye 6 on the epiretinal surface between the vitreous 154 and the neuroretina 150. This RSD embodiment 60 is similar to the RSD 10 of FIGS. 2A and 2B. However, in this preferred RSD embodiment 60, the RSD is secured on the epiretinal surface by retinal tacks 62 or a biocompatible glue as is well known to those skilled in the art. Light 156 entering the eye 6 through the cornea 158 and lens 160 is focused onto the RSD 60. Electric current is generated by the RSD 60 to provide beneficial stimulation to the underlying neuroretina 150. Preferably the stimulation electrode that contacts the neuroretina is a cathode and the ground return electrode of the RSD 60 contacts the vitreous fluid154 is the anode. However, the reversed position of the anode and the cathode is also suitable for electrical stimulation. For purposes of reference, other structures of the eye 6 that are shown are the iris 162, the sclera 164 and the optic nerve 166.

FIG. 8 is a cross-sectional view showing another preferred RSD embodiment 70 implanted in an eye 6 on the anterior scleral surface between the conjunctiva 159 and the sclera 164 preferably nasal or temporal to the cornea. This RSD embodiment 70 is similar to the RSD 10 of FIGS. 2A and 2B. However, in this preferred RSD embodiment 70, the RSD is secured in the subconjunctival space by the conjunctiva 159 on the RSD 70 anterior surface and the sclera 164 on the RSD 70 posterior surface. Light 156 passing through the conjunctiva 159 illuminates the RSD 70. Electric potential is generated by the RSD 70 that provides beneficial stimulation to the neuroretina 150 via conduction through the sclera 164. It is preferred that the stimulation electrode that contacts the sclera 164 is a cathode and the ground return electrode of the RSD 70 that contacts the conjunctiva 159 is the anode. However, the reversed position of the anode and the cathode is also suitable for electrical stimulation. For purposes of reference, other structures of the eye 6 that are shown are the iris 162, the sclera 164 and the optic nerve 166.

In addition to the preferred embodiments of the RSD described above, the devices in Table A are also preferred.

TABLE A

| Device | References |
| --- | --- |
| Artificial Silicon Retina (ASR ™) | (Chow, U.S. Pat. No. 5,016,633, 1991; Chow, U.S. Pat. No. 5,024,223, 1991) |
| Independent Surface Electrode Microphotodiodes (ISEMCP) | (Chow and Chow, U.S. Pat. No. 5,397,350, 1995; Chow and Chow, U.S. Pat. No. 5,556,423, 1996) |
| Independent Surface Electrode Microphotodiodes with an electrical capacitor (ISEMCP-Cs) | (Chow and Chow, U.S. Pat. No. 5,397,350, 1995; Chow and Chow, U.S. Pat. No. 5,556,423, 1996) |
| Multi-phasic Photodiode Retinal Implants (MMRIs, such as MMRI-4) | (Chow and Chow, U.S. Pat. No. 5,895,415, 1999; Chow and Chow, U.S. Pat. No. 6,230,057 B1, 2001) |
| Variable Gain Multi-phasic Photodiode Retinal Implants (VGMMRIs) | (Chow and Chow, US Application No. 09/539,399, 2000) |

Location of Electrical Stimuli

The electrical stimulation, if provided by implants such as the RSDs described above, may be provided subretinally, epiretinally, subsclerally (between the sclera and choroid), on the scleral surface, on the conjuctival surface and/or from or within any structure of the eye. Other means of providing electrical simulation to the retina and eye may include devices that deliver stimulation from the underside of the eyelid(s). Preferably, stimulation is from the subretinal space. Electrical stimulation from the exterior of the eyelid is not preferred.

Implantation Sites and Surgical Methods

In one embodiment, the RSD or RSDs is preferably implanted in the subretinal space in the periphery and/or mid-periphery of the eye, outside of the macula. More than one RSD is implanted, if needed, in an eye to stimulate a larger area of the retina, and multiple RSDs would preferably be implanted in paracentral locations such as one in each of the four paracentral quadrants, approximately, but not limited to, 5 to 80 degrees peripheral to the macula.

FIG. 9 is a cross-sectional view of an eye 6 showing an array 200 of RSDs 10 in the subretinal space. The RSDs may be spaced symmetrically around the macula in the peripheral or mid-peripheral regions of the eye in one embodiment. Alternatively, the RSDs may be spaced asymmetrically around the macula. In one embodiment, the RSDs are implanted at a position in the subretinal space between about a 5 degrees and an 80 degrees angle off-axis from the macula, where the angle is defined by an intersection of an axis line extending from the macula to a central portion of the pupil and an off-axis line extending from the retina stimulation device to the central portion of the pupil. The RSDs may also be implanted in the temporal half retina region and/or nasal half retina region, within the subretinal space. Any of a number of techniques and instruments may be used to perform the implantation into the subretinal space (Chow, U.S. Pat. No. 5,024,223, 1991; Chow and Chow, U.S. Pat. No. 5,397,350, 1995).

In yet another preferred embodiment, the RSD is designed to be implanted onto the epiretinal surface (i.e. on the nerve fiber layer side) of the retina. It is retained in position by retinal tacks, biocompatible glues, or other means known to one skilled in the art. In this embodiment, the photoactive side of the RSD, i.e. the side directed towards incoming light, is the anode of the photodiode. On the opposite side of the RSD chip is the cathode, contacting the nerve fiber layer surface. This preferred embodiment RSD is also implantable in the subconjunctival space on the anterior scleral surface. In this location, the RSD is placed between the conjunctiva and the sclera just nasal, temporal, superior, or inferior to the cornea. From this location, incident light causes electric current to be produced by the RSD that is directed through the sclera into the retina by the contacting scleral cathode. The preferred locations are nasal and temporal to the cornea. The electrical ground return is at the anode and is in contact with the underside of the conjunctiva. Although the subconjunctival/scleral placement of the RSD results in less efficient electrical stimulation of the retina compared to a subretinally or epiretinally placed RSD, the extraocular location of a RSD decreases the surgical risk to a patient since intraocular surgery would not be required for its implantation. The subconjunctival/scleral placement of a RSD also allows a stable RSD position to be achieved without fixating devices or glues (i.e., the device is held in place between the conjunctiva and sclera) used to secure epiretinal RSDs.

Surgical methods are well known in the art (Peyman et al., 2000). Descriptions of specific surgeries for RSD implantation have been extensively described (Chow, U.S. Pat. No. 5,024,223, 1991; Chow and Chow, U.S. Pat. No. 5,397,350, 1995; Chow and Chow, U.S. Pat. No. 5,556,423, 1996; Chow and Chow, 1997; Chow et al., 2001; Chow and Peachey, 1999; Chow and Chow, U.S. Pat. No. 5,895,415, 1999; Chow and Chow, U.S. Pat. No. 6,230,057 B1, 2001).

For example, direct insertion may be accomplished as follows: the RSD (or a plurality of RSDs) is inserted into the vitreous cavity of the eye through a pars plana incision. A horizontal incision is then made through the retina from the vitreous side in the temporal portion of the posterior pole into the potential space between the photoreceptor layer and the retinal pigment epithelium. A horizontal incision made at this location avoids cutting inner retinal vasculature and is parallel to coursing nerve fiber layers, therefore also avoiding their injury. Illumination for surgery is provided by an optical fiber light pipe. The potential space is then be opened by cannula irrigation of a balanced salt solution into the subretinal space.

The device is then placed into the subretinal cavity at the posterior pole under the macula area. Specifically, the device is placed between the retinal pigment epithelium and photoreceptor layer, or if the photoreceptor layer is atrophied or lost, then between the retinal pigment epithelium and the bipolar and horizontal cell layer. The device is positioned such that the electrical ground(s) is overlaying the retinal pigment epithelium, and the active electrode(s) faces incident light.

After insertion, a series of endolaserphotocoagulation or endocautery burns may be made around the periphery of the device to secure the device, although these burns may not be necessary in many cases. The scar tissue so formed around the periphery of the device by these burns may prevent the device from moving out of position in some patients. Endolaserphotoco-agulation or endoelectrocautery may also be used to seal the retinal incision. Air or other medically approved gaseous compounds may also be injected into the vitreous cavity to tamponade the retinal opening during healing. The pars plana incision is then closed in the usual surgical manner.

An alternate method for implantation of the RSD involves making an incision through the sclera just posterior to the ora serata. Dissection proceeds through the choroid, choriocapillaris, Bruch's membrane and retinal pigment epithelium under stereo operating microscope control into the potential space between the inner and outer anatomical retinal layers. The artificial retinal implant is then inserted into this space and directed posteriorly towards the macula by a pushing action imparted by a formed curved iris spatula or by use of an insertion guide. The RSD rests in the retinal periphery of the eye between the inner and outer anatomical retinal layers.

In another approach, some devices can be implanted by simple injection into the subretinal space through cannulas. Preferably, the RSDs are placed in a vehicle such as a biocompatible liquid and injected into the subretinal space via a retinotomy incision using a cannula. Such a liquid vehicle may be a balanced salt solution or a more viscous material like methylcellulose.

The retina is preferably illuminated by a light pipe to facilitate the injection of the RSDs. The cannula is introduced into the vitreous cavity of the eye via a pars plana incision. Dissection of the posterior vitreous is performed to separate the posterior hyaloid face from the retinal surface along with a vitrectomy. A small retinotomy incision is made through the retina following the direction of the nerve fiber layer using a stiletto type MVR blade. Dissection of the inner retina from the outer retinal layers is accomplished hydrostatically with the cannula using a fluid such as saline.

When the retinal areas to be implanted have been prepared with cannula hydro-dissection, the liquid vehicle with suspended RSDs is injected. An attempt should be made to distribute the suspended RSDs in a uniform monolayer. The cannula is then withdrawn, and a heavier-than-water nonmiscible material (preferably, a perfluorocarbon) is placed over the posterior pole of the vitreous cavity to aid settling the retina. The non-miscible material is preferably removed after an appropriate time, usually 15 to 20 minutes, leaving a reattached retina. Alternatively, air may also be used to settle the retina. With settling and reattachment of the retina, the implanted RSDs tend to distribute into the desired monolayer.

Other surgical procedures and related materials will be evident to one of skill in the art and depend in part on the design of the RSD and the subject to be implanted.

Growth Factors

In addition to the endogenous retinal growth factors that are produced and released by electrical stimulation of retina cells by the methods of the invention, growth factors can also be instilled into the eye that further enhance retinal rescue and retina functional improvement. This additional step is attractive because Injecting growth factors, especially neurotrophic-type growth factors, have been reported to improve retinal function and provide limited neuronal rescue in eyes with retinal degeneration and dysfunction. These growth factors include, but are not limited to, glial cell line-derived neurotrophic factor (GDNF), nerve growth factor (NGF), brain derived neurotrophic growth factor (BDNGF), neurotropin-3 (NT-3), neurotropin-4 (NT-4), neurotropin-5 (NT-5), ciliary neurotropic factor (CNTF) and fibroblastic growth factor (FGF). These growth factors can be delivered to the eye by coating the RSD with growth factor(s) before implantation, by injection of the growth factor(s) into the locations of the subretinal space, vitreous cavity, subconjunctival space, subscleral space, and/or the anterior chamber either singly or in combination with each other, as a single dose or as multiple repeat doses before, during and/or after implantation of the RSD(s) or other electrical stimulating device.

Amplitude, Pattern and Frequency of Stimulation

Using the preferred RSDs, electrical stimulation is generated upon exposure to visible and/or infrared light (400 to greater than 750 nm); in the case of MMRIs, the NIP configuration provides a current when illuminated with visible light (400–750 nm), while the PIN configuration provides a current when illuminated with infrared light (greater than 750 nm). The RSDs, however, may be designed to respond to any wavelength or wavelength portions of ultraviolet, visible and/or infrared light, using methods and designs such as those described (Chow and Chow, U.S. Pat. No. 6,230,057 B1, 2001) and to produce any temporal pattern of stimulation. For example, the produced current per RSD may be 0.01 nA to 2,000,000 nA; most preferably 1 to 5000 nA and the temporal pattern of stimulation may be monophasic, biphasic or complex combinations of monophasic and biphasic waveforms with varying ramps of increasing and decreasing current and voltage. Electrical stimulation may also be provided continuously or intermittently. The electric current output of the RSD will depend on the degree of RSD stimulation by the appropriate light wavelengths or wavelength portions of light. The voltage potential of the RSD output is −20V to +20V, preferably −5V to +5V, and most preferably −1V to +1V.

Demonstration of Efficacy

The demonstration of safety and efficacy of a preferred embodiment of this invention has been shown in multiple persons with retinal dysfunction that have been implanted with RSDs in the subretinal space as part of a clinical study to evaluate the feasibility of and effectiveness of these devices to act as prostheses. All persons so implanted have reported no complications and have reported improved levels of visual function subsequent to the placement of the RSDs. Such improvements have included improved perception of light, darkness, contrast, shape, resolution, color, motion, and visual field size. It will be appreciated by those of skill in the art that the improved levels of visual function reported represent results of RSDs and methods discovered by the inventors to function well in the practice of the invention. However, those skilled in the art should, in light of the present disclosure, appreciate that many changes can be made in the specific embodiments that are disclosed and still obtain a like or similar result without departing from the spirit and scope of the invention.

Equivalents

Although particular embodiments have been disclosed herein in detail, this has been done for purposes of illustration only and is not intended to be limiting with respect to the scope of the appended claims that follow. In particular, it is contemplated by the inventors that various substitutions, alterations, and modifications may be made to the invention without departing from the spirit and scope of the invention as defined by the claims. Other aspects, advantages, and modifications are considered to be within the scope of the following claims.

The invention claimed is:

1. A method of improving visual function of a damaged retina in a human eye, the method comprising:
    applying electrical stimulation to the eye with a source of electrical stimulation to improve visual function of the damaged retina, wherein applying electrical stimulation improves visual function of at least one structure of the damaged retina not in contact with the source of electrical stimulation, and wherein the electrical stimulation comprises a voltage potential, $V_p$, of $-20V \leq V_p \leq +20V$.

2. The method of claim 1, wherein the $V_p$ is $-5V \leq V_p \leq +5V$.

3. The method of claim 1, wherein the $V_p$ is $-1V \leq V_p \leq +1V$.

4. The method of claim 1, wherein said electrical stimulation is intermittent.

5. A method of treating visual degradation resulting from a damaged retina, wherein the visual degradation comprises primary or secondary degradation, the method comprising:
    applying electrical stimulation to an eye containing the damaged retina with a source of electrical stimulation, wherein a portion of the damaged retina not in contact with the source of electrical stimulation is treated, and wherein the electrical stimulation comprises a voltage potential, $V_p$, of $-20V \leq V_p \leq +20V$.

6. The method of claim 5, wherein the $V_p$ is $-5V \leq V_p \leq +5V$.

7. The method of claim 5, wherein the $V_p$ is $-1V \leq V_p \leq +1V$.

8. The method of claim 5, wherein the electrical stimulation is intermittent.

* * * * *